US006582941B1

(12) United States Patent
Yokochi et al.

(10) Patent No.: US 6,582,941 B1
(45) Date of Patent: Jun. 24, 2003

(54) MICROORGANISMS CAPABLE OF PRODUCING HIGHLY UNSATURATED FATTY ACIDS AND PROCESS FOR PRODUCING HIGHLY UNSATURATED FATTY ACIDS BY USING THE MICROORGANISMS

(75) Inventors: Toshihiro Yokochi, Tsukuba (JP); Toro Nakahara, Tsukuba (JP); Takanori Higashihara, Tsukuba (JP); Satohiro Tanaka, Shiso-gun (JP); Toshiaki Yaguchi, Ibaraki (JP)

(73) Assignees: Japan as represented by Director-General of Agency of Industrial Science and Technology, Tokyo (JP); Suntory Limited, Osaka (JP)

( * ) Notice: Subject to any disclaimer, the term of this patent is extended or adjusted under 35 U.S.C. 154(b) by 0 days.

(21) Appl. No.: 08/945,226

(22) PCT Filed: Apr. 17, 1996

(86) PCT No.: PCT/JP96/01049

§ 371 (c)(1),
(2), (4) Date: Dec. 29, 1997

(87) PCT Pub. No.: WO96/33263

PCT Pub. Date: Oct. 24, 1996

(30) Foreign Application Priority Data

Apr. 17, 1995 (JP) .............................................. 7-115183
Sep. 14, 1995 (JP) .............................................. 7-236669
Oct. 12, 1995 (JP) .............................................. 7-263921

(51) Int. Cl.$^7$ .............................. C12N 1/14; C12P 7/64; A23K 1/16; A23L 1/30; C11C 3/00

(52) U.S. Cl. .......................... 435/134; 424/490; 426/33; 426/34; 426/98; 426/648; 426/42; 435/254.1; 435/911; 435/134; 435/946; 514/547; 554/219; 554/224

(58) Field of Search .............................. 435/254.1, 911; 426/33, 34, 98, 648; 514/547; 554/219, 224; 424/490

(56) References Cited

U.S. PATENT DOCUMENTS

| 4,701,468 A | 10/1987 | Mendy et al. .............. 514/547 |
| 5,130,242 A | 7/1992 | Barclay ...................... 435/134 |
| 5,340,594 A | 8/1994 | Barclay ........................ 426/49 |
| 5,340,742 A | 8/1994 | Barclay .................... 435/256.8 |
| 5,518,918 A | 5/1996 | Barclay .................... 435/257.1 |
| 5,539,133 A | 7/1996 | Kohn et al. .................... 554/20 |
| 5,656,319 A | 8/1997 | Barclay ...................... 426/574 |
| 5,688,500 A | 11/1997 | Barclay .................... 424/93.1 |
| 5,698,244 A | 12/1997 | Barclay .......................... 426/2 |

FOREIGN PATENT DOCUMENTS

| DE | 42 19 360 | 12/1993 |
| DE | 43 27 310 | 2/1994 |
| EP | 0 157 619 | 10/1985 |
| EP | 0 222 169 | 5/1987 |
| EP | 0 304 603 | 3/1989 |
| EP | 0 404 058 | 12/1990 |
| EP | 0 440 308 | 8/1991 |
| EP | 0 594 862 | 5/1994 |
| EP | 0 609 056 | 8/1994 |
| EP | 0 611 528 | 8/1994 |
| EP | 0 615 753 | 9/1994 |
| JP | 59-190948 | 10/1984 | ......... C07C/69/003 |
| JP | 01180849 | 7/1989 | ........... C07C/57/03 |
| JP | 05276963 | 10/1993 | ............. C12P/7/64 |
| JP | 05308978 | 11/1993 | ............. C12P/7/64 |
| WO | 94/08467 | 4/1994 |
| WO | 94/28913 | 12/1994 |

OTHER PUBLICATIONS

APS Abstract JP08–336360 Yazawa et al "Feed Compositions for Ruminant and Feeding Using the same" Dec. 24, 1996.*
Kendrick A. et al: "Lipids of Selected Molds Grown for Production on N–3 and N–6 Polyunsaturated Fatty Acids", Lipids, vol. 27, No. 1, Jan. 1, 1992, pp. 15–20.
Ellenbogen B.B. et al.: "Polyunsaturated Fatty Acids of Aquatic Fungi: Possible Phylogenetic Significance", Comparative Biochemistry and Physiology, vol. 29, 1969, pp. 805–811.
Nakahara T. et al.: "Production of Docosahexaenoic and Docosapentaenoic Acids by Scghizochytrium sp. Isolated from Yap Islands", Journal of the American Oil Chemists' Society, vol. 73 No. 11, Nov. 1966, pp. 1421–1426.

(List continued on next page.)

Primary Examiner—Herbert J. Lilling
(74) Attorney, Agent, or Firm—Jacobson Holman PLLC

(57) ABSTRACT

The present invention relates to the Schizochytrium genus SR21 strain and a microorganism belonging to the same species as does said SR21 strain or having substantially the same fungological properties as does said SR21 strain, the said SR21 strain and microorganism having the ability to produce the (n-3) series of docosahexaenoic acid (DHA) and the (n-6) series of docosapentaenoic acid (DPA), and the invention also relates to a process for preparing the (n-3) series of DHA and the (n-6) series of DPA utilizing said microorganisms. The microorganisms according to the present invention are superior in their proliferation character and their propensity to produce fat, and have the ability to produce the (n-3) series of DHA and the (n-6) series of DPA very well. Accordingly, it is possible to effectively produce the (n-3) series of DHA and/or the (n-6) series of DPA, which are useful in the fields of foods and pharmaceuticals, using the microorganisms according to the present invention. In addition, the present invention provides a fat obtained by culturing the present microorganisms. Since the fat composition contains the (n-6) series of DPA in addition to the (n-3) series of DHA having various physiological activities, it is possible to stably and effectively supply the (n-6) series of DPA and/or the (n-3) series of DHA to subjects in need of these highly unsaturated fatty acids by adding the fat composition to various feedstuffs or foods.

46 Claims, 5 Drawing Sheets

OTHER PUBLICATIONS

Kendrick et al., "Lipids of Selected Molds Grown for Production on N–3 and N–6 Polyunsaturated Fatty Acids", Lipids, vol. 27, No. 1, Jan. 1, 1992, pp. 15–20.

Ellenbogen et al., "Polyunsaturated Fatty Acids of Aquatic Fungi: Possible Phylogenetic Signifcance", Comparative Biochemistry and Physiology, vol. 29, 1969, pp. 805–811.

Nakahara et al., "Production of Docosahexaenoic and Docosapentaenoic Acids by Schizochytrium Sp. Isolated from Yap Islands", Journal of the American Oil Chemists' Society, vol. 73, No. 11, Nov. 1996, pp. 1421–1426.

Patent Abstracts of Japan, vol. 013, No. 529 (C–658), Nov. 27, 1989 & JP 01 215245 A (Suntory Ltd), Aug. 29, 1989.

Napolitano et al., "Fatty Acid Composition of Three Cultured Algal Species (Isochrysis Galbana, Chaetoceros Gracilis and Chaetoceros Calcitrans) used as food for Bivalve Larvae", Journal of the World Aquaculture Society, vol. 21, No. 2, Jun./1990, pp. 122–130.

Mieth et al., "Zur Lipidzusammensetzung von Plankton als Futterquelle von Silber–und Marmorkarpfen 1. Mitt. Fettsaurespektrum Verschiedener Lipidklassen", Die Nahrung, vol. 36, No. 1, 1992, pp. 90–92.

Database WPI, Week 199424, Derwent Publications Ltd., London, GB, An 1994–197416 & JP 06 136394 A (Biox KK.; Sagami Chem. Res. Ctr.).

Database WPI, Week 199345, Derwent Publications Ltd., London, GB, An 1993–357130 & JP 05 262639 A (Johnson & Johnson KK.).

* cited by examiner

MICROORGANISMS CAPABLE OF PRODUCING HIGHLY UNSATURATED FATTY ACIDS AND PROCESS FOR PRODUCING HIGHLY UNSATURATED FATTY ACIDS BY USING THE MICROORGANISMS

TECHNICAL FIELD

The present invention relates to the Schizochytrium genus SR21 strain and a microorganism belonging to the same species as does said SR21 strain or having substantially the same fungological properties as does said SR21 strain, the said SR21 strain and microorganism having the ability to produce a fat containing the (n-3) series of docosahexaenoic acid and the (n-6) series of docosapentaenoic acid, and the invention also relates to a process for preparing the (n-3) series of docosahexaenoic acid and/or the (n-6) series of docosapentaenoic acid utilizing said microorganisms.

In addition, the present invention relates to the fat produced by the above microorganisms, various feedstuffs and foods supplemented with the fat, as well as a process for utilizing the fat as an additive for various feedstuffs and foods.

BACKGROUND ART

It is believed that highly unsaturated fatty acids such as docosahexaenoic acid (DHA) and docosapentaenoic acid (DPA), have a variety of physiological activities in animal bodies. It is known that these highly unsaturated fatty acids are divided into the (n-3) series and (n-6) series owing to the difference in the positions of their unsaturated bonds. In animal bodies, the (n-3) and (n-6) series of the highly unsaturated fatty acids belong to different metabolic pathways, and animals require both the acids as essential fatty acids.

The (n-3) series of highly unsaturated fatty acids include, for example, eicosapentaenoic acids [20:5 (n-3)], docosahexaenoic acid [22:6 (n-3)] or the like. It is known that these fatty acids have a physiological activity, such as anti-inflammatory or anti-thrombotic activity, and they are noted as a material for functional foods or for pharmaceuticals.

On the other hand, the (n-6) series of highly unsaturated fatty acids include, for example, γ-linolenic acids [18:3 (n-6)], di-homo-γ-linolenic acid [20:3 (n-6)], arachidonic acid [20:4 (n-6)] or the like, and they are noted as an intermediary metabolite toward the first or second group of eicosanoids, such as prostaglandins, leucotrienes or the like, which are referred to as local hormones.

In animal bodies, the final metabolite of the (n-3) series is docosahexaenoic acid and that of the (n-6) series is arachidonic acid, although they vary depending on tissues. For example, the fatty acid composition of phospholipids in human erythrocytes is as follows: for the (n-3) series, 0.70% eicosapentaenoic acid, 2.09% docosapentaenoic acid, 4.37% docosahexaenoic acid; on the other hand, for the (n-6) series, 12.67% linoleic acid, 0.62% di-homo-γ-linolenic acid, 16.93% arachidonic acid, 0.86% docosapentaenoic acid [Hardy et al., Biochem. J., vol. 274, p. 133 (1991)]. Thus, the amount of the (n-6) series of docosapentaenoic acid is very low.

The (n-3) series of docosahexaenoic acid (DHA) which is the final metabolite of the (n-3) series is present specifically in the brain or retina of animals, and it is believed that it performs some function in these organs. The (n-3) series of DHA is contained in oil from fish belonging to the group of blue fish, and in particular, contained in the oil from sardines or tuna in an amount of around 20%. Recently, due to the discovery of fish material containing a high concentration of DHA, such as the orbital fat of tuna, due to the progress of technology for purifying fatty acids well, and also due to other things, intensive efforts have been made to elucidate the physiological functions of DHA and to investigate its practical use. It has become apparent that DHA has physiological functions, such as an effect in lowering cholesterol, an anticoagulant effect and a carcinostatic effect. In relation to the brain metabolic system, it has also become apparent that DHA is effective for improving memory and learning ability, preventing senile dementia and treating Alzheimer's disease. In addition, it has been proved that DHA is an essential fatty acid for the growth of fry. For reasons of the above, DHA is used as a material for health foods, baby milks or the like.

On the other hand, it is believed that the content of the (n-6) series of docosapentaenoic acid (DPA) in animal bodies increases in compensation for a lack of the (n-3) series of essential fatty acids. For example, in the fatty acid composition in optic nerve choroidea plexus of rats in the third generation after continuously receiving feed containing safflower oil which is very rich in the (n-6) series of fatty acids, the (n-3) series of DHA decreases to the degree of ⅓, while the (n-6) series of DPA increases 4 times [Homayoun et al., J. Neurochem., vol. 51, p. 45 (1988)]. Furthermore, it has been reported that the content of the (n-6) DPA in the hepatic microsome of rat having deficiency of vitamin A sharply increases from a normal value of 0.9% to 10.5% [Hamm et al., Biochem. J., vol. 245, p. 907 (1987)], that the (n-3) DHA decreases and the (n-6) DPA increases in rat receiving palm oil which is poor in components of the (n-3) series [Rebhung et al., Biosci. Biotech. Biochem., vol. 58, p. 314 (1994)], and so on.

Thus, the fact that the (n-6) DPA is produced in vivo in compensation for the (n-3) DHA which is suspected to perform a function in the brain or retina of animals suggests that the (n-6) DPA has a physiological role. In addition, the (n-6) DPA can be expected to be an antagonist to arachidonic acid.

Moreover, the following use of the (n-6) DPA is known at present: use of the same as a carrier for providing a tendency toward the easy transport of tranquilizer into the brain [Japanese Patent Publication (Kokai) No. 204136/1986] as well as use of the same in combination with the (n-6) series of docosatetraenoic acid for treating diseases in which the content of the (n-6) series of unsaturated fatty acids containing 22 carbon atoms is reduced from the normal level, for example, infection with a virus, in particular wart virus; leukemia, breast carcinoma and the other type of carcinomas; premenstrual syndrome and benign pectoral diseases; hypertension, hyperlipemia and obesity, dry eye syndrome; scleroderma, rheumatoid arthritis, Crohn disease, ulcerative colitis and the other type of autoimmune and inflammatory diseases; infertility; diabetes; psychotic diseases including schizophrenia and alcoholism (including influences of both excessive drinking and withdrawal effects) [Japanese Patent Publication (Kokai) No. 38324/1985].

The (n-6) DPA is not contained at all in fats usually supplied, but contained only in a small amount in fish oil together with the (n-3) DPA. Although a patent application directed to a process for isolating and/or concentrating the (n-6) DPA from the fish oil has been filed [Japanese Patent Publication (Kokai) No. 180849/1989], it is difficult to efficiently isolate and/or concentrate the same because the content of the (n-6) DPA in the fish oil is as little as 1%, the fish oil predominantly contains highly unsaturated fatty acids having a structure similar to that of the (n-6) DPA such as arachidonic acid, eicosapentaenoic acid or docosahexaenoic acid, and the (n-3) DPA is contained in a content a few times higher than the (n-6) DPA, and therefore, the process requires, for example, a multistage chromatography treatment.

As described above, fish oil contains the (n-3) DHA and (n-6) DPA which have noteworthy physiological functions, but a fat containing these (n-3) DHA and (n-6) DPA in a large amount is not yet known. Furthermore, if one intends to use the fish oil, several disadvantages exist, such as the inability to maintain a stable source of fish oil due to the migration of fish or the like, or the offensive odor inherent in fish oil. Also, it is difficult to obtain a fat of reliable quality, because fish oil also contains highly unsaturated fatty acids, such as arachidonic acid (AA) and eicosapentaenoic acid (EPA), and is therefore easily oxidized. In addition, if one intends to obtain a highly purified (n-3) DHA or (n-6) DPA, it is difficult to separate and purify the same. In particular, when adding to a baby milk, it is desirable that the content of eicosapentaenoic acid is low, but it is very difficult to efficiently remove only eicosapentaenoic acid when using fish oil as the source.

Besides fish oil, fat accumulated in cultured cell bodies of a microorganism having the ability to produce the (n-3) series of docosahexaenoic acid is known as a source of the (n-3) series of docosahexaenoic acid. For example, the following microorganisms are known as those having the ability to produce the (n-3) series of docosahexaenoic acid: a bacterium separated from the deep sea, Vibrio marinus (ATCC 15381); Vibrio bacteria separated from the intestines of a deep-sea fish; micro-algae, Cyclotella cryptica and Crypthecodinium cohnii [Japanese Patent Publication (Kohyo) No. 503425/1993]; flagellate fungi, Thraustochytrium aureum (ATCC 34304) [Kendrick, Lipids, vol. 27, p. 15 (1992)] and Japonochytrium sp. (ATCC 28207) [Japanese Patent Publication (Kokai) No. 199588/1989]. According to a process utilizing these microorganisms, however, the amount of docosahexaenoic acid produced per liter (L) of medium is only on a very low level and in the order of several tens to 500 mg.

On the other hand, some of the micro-algae produce a fat containing docosapentaenoic acid, but the docosapentaenoic acid produced by each of these microorganisms is that of the (n-3) series. In addition, it is known that docosapentaenoic acid is also contained in flagellate fungi, Thraustochytrium aureum (ATCC 34304), Japonochytrium sp. (ATCC 28207) or the like, but it is reported that the acid produced by these microorganisms is also that of the (n-3) series. Thus, it was not previously known that the (n-6) series of docosapentaenoic acid is contained in the fat produced by these microorganisms in a sufficient amount.

DISCLOSURE OF INVENTION

The present inventors extensively sought a microorganism in marine microorganisms which produces much of a fat having a high content of the (n-3) series of docosahexaenoic acid (DHA) and/or the (n-6) series of docosapentaenoic acid (DPA) as mentioned above and having a low content of eicosapentaenoic acid (EPA).

As a result, they found that a certain kind of marine microorganism (assigned to a new species belonging to the Schizochytrium genus) produces much of a fat which contains not only the (n-3) DHA in a high content but also the (n-6) DPA and contains EPA in a low content, and thus they achieved the present invention.

Thus, the present invention provides the Schizochytrium genus SR21 strain and a microorganism belonging to the same species as does said SR21 strain or having substantially the same fungological properties as does said SR21 strain, the said SR21 strain and microorganism having the ability to produce a fat containing the (n-3) series of docosahexaenoic acid (DHA) and the (n-6) series of docosapentaenoic acid (DPA).

Also, the present invention provides a process for preparing a fat containing the (n-3) series of DHA and the (n-6) series of DPA, characterized in that the above microorganism is cultured and the above fat is recovered from the culture.

Furthermore, the present invention provides a process for preparing the (n-3) series of DHA or the (n-6) series of DPA, characterized in that it further encompasses a step of isolating the (n-3) series of DHA or the (n-6) series of DPA from the above fat.

In addition, the present inventors found that the above fat is useful as a source of the (n-3) DHA and/or (n-6) DPA for various feedstuffs and foods.

Thus, the present invention provides various feedstuffs and foods supplemented with the above fat.

Also, the present invention provides a process for utilizing the above fat as an additive for various feedstuffs and foods.

BEST MODE FOR CARRYING OUT THE INVENTION

The present invention is further described in the following.

In this context, the terms "fat", "lipid" and "oil" described in the specification are used having the same meaning.

The marine microorganism, SR21 strain according to the present invention was isolated from sea water taken in the coast of Yap Island in Micronesia. Initially, the strain was believed to be a microorganism belonging to the Thraustochytrium genus. However, as a result of detailed investigation of the fungological characteristics of the strain, it was found that the strain was a microorganism recognized as a new species belonging to the Schizochytrium genus. The fungological characteristics of the Schizochytrium genus SR21 strain are as follows.

The fungological characteristics of the SR21 strain were investigated by culturing it in a nutrient medium and in sea water.

A nutrient medium prepared by adding 2 g of glucose, 0.2 g of yeast extract and 0.5 g of sodium glutamate to 1 L of artificial sea water (tropic marine) was first charged into a small dish, the dish was inoculated with one drop of a pre-culture of the SR21 strain prepared in a flask using the same medium, and the morphology of cells was traced with an invert microscope. In this case, the release of amoebic irregular-shaped cells was observed.

Next, a similar trace was carried out in natural sea water sterilized with a filter. In this case, the release of amoebic irregular-shaped cells was not observed, but release of zoospores from several cells in a vegetative cell mass formed after repeating binary fission was observed. Cells which directly differentiated from a single vegetative cell to a zoospore without binary fission were also observed.

Glutaraldehyde was added in an amount of 10% by volume to a sample where the release of zoospores was often observed, and the observation of the zoospores was carried out using an optical microscope.

Figure 1:
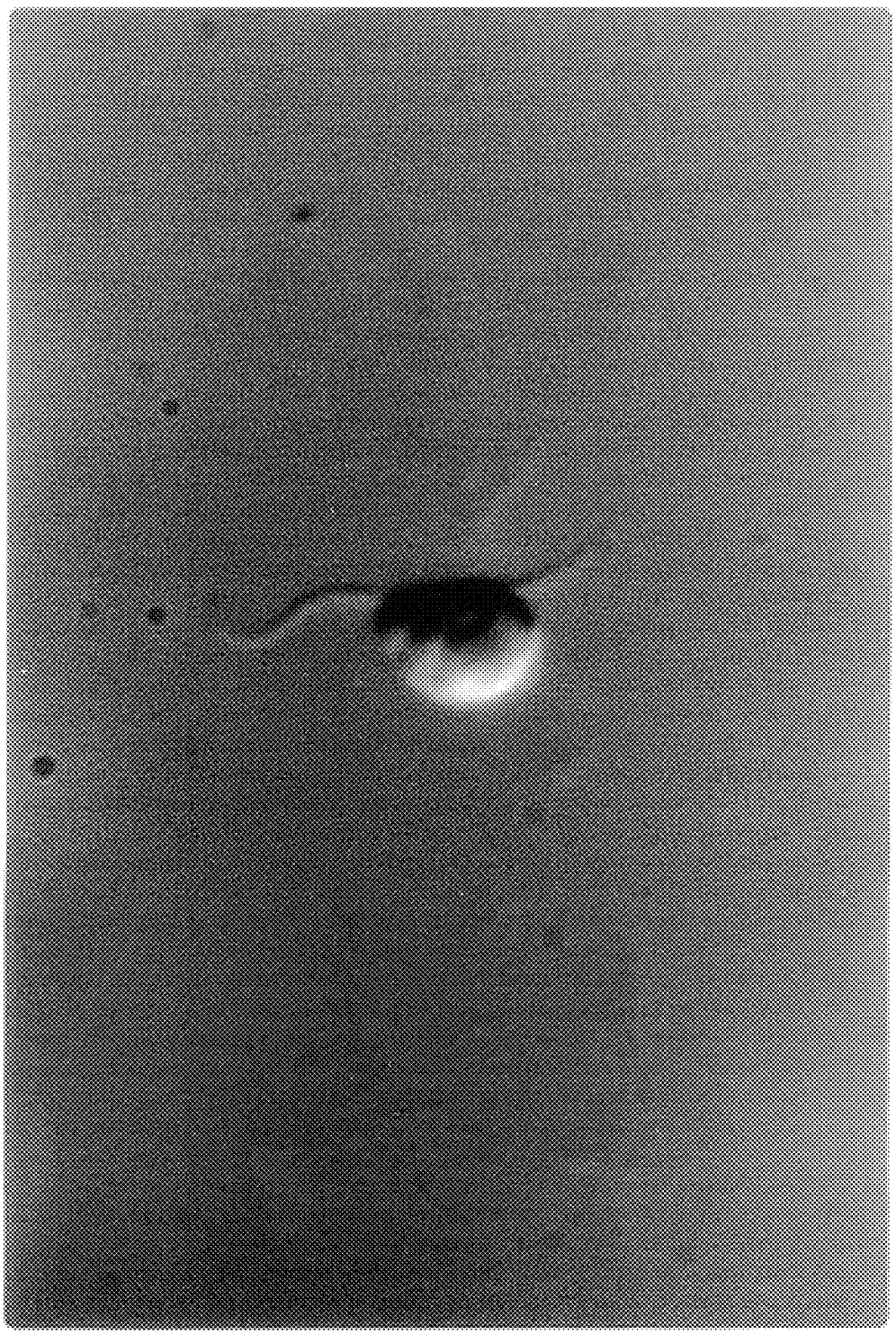
FIG. 1 is an optical micrograph showing the morphology of a zoospore of the Schizochytrium genus SR21 strain.

FIG. 1 is an optical micrograph showing the morphology of a zoospore of the SR21 strain, which shows two flagella different in length.

Figure 2:
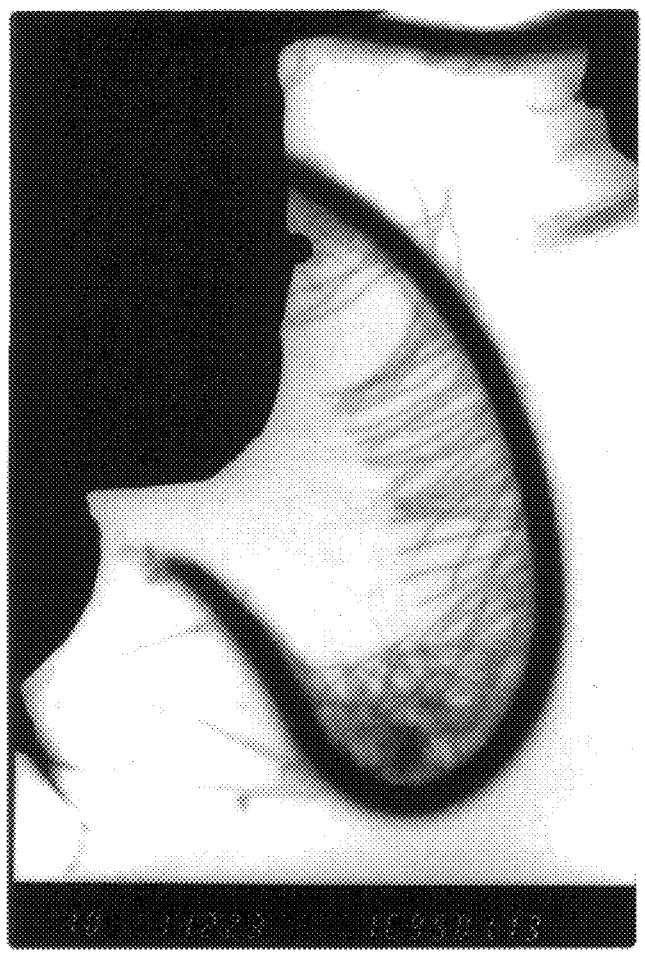
FIG. 2 is a transmission electron micrograph showing the structure of flagella of a zoospore of the Schizochytrium genus SR21 strain.

Moreover, observation of the flagella using an electron microscope was carried out by a negative staining method using uranium acetate. FIG. 2 is a transmission electron micrograph showing the structure of flagella of a zoospore of the SR21 strain, which shows a three part-structure of mastigonemes of the flagellum consisting of proximal part, axial part and terminal hair.

Figure 3:
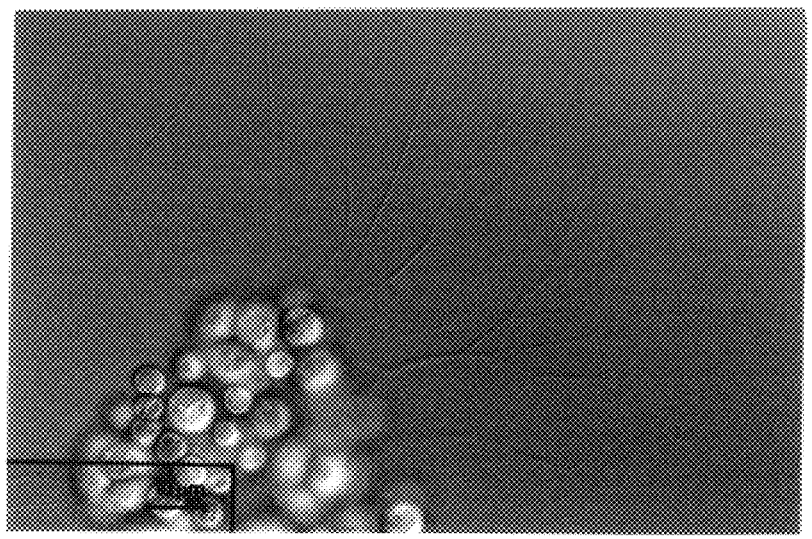
FIG. 3 is an optical micrograph showing the network between a vegetative cell mass and plasma of the Schizochytrium genus SR21 strain.

Furthermore, after the vegetative cells repeated binary fission, the formation of a network between the vegetative cell mass and plasma was seen in the above two observations of the cell morphology by an invert microscope. FIG. 3 is an optical micrograph showing the network between the vegetative cell mass and plasma of the SR21 strain.

The colony formed by the SR21 strain on an agar plate medium exhibited a smooth and mud yellow color similar to that of a colony of yeast. Furthermore, when the SR21 strain was grown in a liquid medium, a zoospore having two flagella different in length was observed in the early stage (FIG. 1) and the filamentous structure (mastigonemes) present on a longer flagellum of the two flagella took a three-part structure consisting of a proximal part, axial part and terminal hair (FIG. 2). From these facts, it is apparent that the SR21 strain belongs to the Kingdom of Chromista and the Phylum of Heterokonta. Moreover, from the characteristic of forming the network of plasma and from a scale derived from the Golgi's body, it is apparent that the SR21 strain belongs to the Class of Labyrinthulea and the Order of Labyrinthulida. In addition, from the facts that the vegetative cells are spherical or oval and that there is no gliding movement in the network of plasma, it is apparent that the SR21 strain belongs to the Family of Thraustochytriidae.

Furthermore, the vegetative cells of the SR21 strain repeat binary fission and form a vegetative cell mass of 8 to 32 vegetative cells. Then, amoebic irregular-shaped cells are released from some of the vegetative cells, which gradually leave the vegetative cell mass and become spherical cells after 1 to 2 hours. The spherical cells then serve as zoosporangia and differentiate into 8 to 16 zoospores. In this case, membranes of zoosporangia are not observed. In addition, cells are observed in which a single vegetative cell directly differentiates into a zoosporangium without binary fission, and cells are also observed in which a vegetative cell forms a vegetative cell mass by binary fission and then the mass differentiates into zoospores without going through the irregular-shaped cells. Thus, the SR21 strain has a complex life cycle.

According to D. Porter ["Handbook of Protoctista", Jones and Bartlett Publishers (1990)], the Thraustochytriidae family consists of seven genera and thirty species. Thereafter, the Corallochytrium genus [Raghukumar, S., Botanica Marina, 30: 83 (1987)] was added to the family, and, according to S. T. Moss ["The Biology of Free-living Heterotrophic lagellates", Oxford University Press (1991)], it is recognized that the family consists of eight genera and thirty-three species.

The characteristics of these eight genera constituting the Thraustochytriidae family are as follows. The vegetative cells of microorganisms belonging to the Labyrinthuloides genus are spherical, but glide irregularly over a network of plasma. Microorganisms belonging to the Aplanochytrium genus grow via aplanospores, i.e., spores having no flagellum. Microorganisms belonging to the Althornia genus do not form a network of plasma and are planktonic. Microorganisms belonging to the Japonochytrium genus produce apophysis on the outside of cells. In microorganisms belonging to the Ulkenia genus, amoebic irregular-shaped cells are released from zoosporangia after which the cells differentiate into zoospores. In microorganisms belonging to the Thraustochytrium genus, one zoospore grows to one vegetative cell and the cell forms one zoosporangium. In microorganisms belonging to the Schizochytrium genus, binary fission is performed after the attachment of a zoospore, whereby a mass consisting of a number of vegetative cells is formed and each becomes zoosporangium. Microorganisms belonging to the Corallochytrium genus form a spore having the morphology of a carapace slug (a species of the Limacidae family) and do not form a zoospore having a flagellum.

In this context, as to the Ulkenia genus among the above eight genera, A. Gaertner [Veroff. Inst. Meeresforsch. Bremerh., 16: 139 (1977)] used, as a criterion for the classification of the genus, the character in which a bare plasma mass (an amoebic irregular-shaped cell) is released from a zoosporangium after which the mass differentiates into zoospores, and he proposed the new genus Ulkenia consisting of six species, by transferring two species, *Thraustochytrium visurgense* [Ulken, A., Veroff. Inst. Meeresforsch. Bremerh., 9: 289 (1965)] and *Thraustochytrium amoeboidum* [Bahnweg, O. and Sparrow, F. K., Jr. Am. J. Bot., 61: 754 (1974)], which had been previously classified into the Thraustochytrium genus, to the Ulkenia genus, and by adding thereto the new species *Ulkenia minuta* described by S. Raghukumar [Veroff. Inst. Meeresforsch. Bremerh., 16: 158 (1977)] and a further three new species.

Thereafter, however, there was no paper describing a new species belonging to the Ulkenia genus. J. S. Karring ["Predominantly Holocarpic and Eucarpic Simple Biflagellate Phycomycetes", J. Cramer (1981)] doubted whether the Ulkenia genus could exist as an independent genus, and mentioned the genus as a provisional one. However, the above description is seen in the literature of Porter and Moss.

Since the SR21 strain forms amoebic irregular-shaped cells, it may be believed that the strain belongs to the Ulkenia genus when attaching importance to the character. However, Raghukumar reported that *Thraustochytrium striatum* belonging to the Thraustochytrium genus formed amoebic irregular-shaped cells in a nutrient medium, which took bacteria [Marine Biology, 113: 165 (1992)]. Furthermore, Raghukumar showed that *Schizochytrium mangrovei* assigned to be a new species belonging to the Schizochytrium genus formed amoebic irregular-shaped cells in a nutrient medium, but it did not form the amoebic irregular-shaped cells when cultured in a medium poor in nutrients such as that prepared by adding only pine pollen to sea water [Trans. Br. Mycol. Soc., 80: 627 (1988)].

Accordingly, Raghukumar thought that it was necessary to investigate the above character using a criterial medium in view of the fact that the character of forming the amoebic irregular-shaped cells was influenced by a medium composition and culture conditions. He mentioned the above sea water/pine pollen medium as a criterial medium, which had been traditionally and often used until then and had been frequently used until then in observing morphology and character in the original description of genera and species. It is known that all six species classified into the Ulkenia genus form amoebic irregular-shaped cells in the sea water/pine pollen medium. On the other hand, *Thraustochytrium striatum* and *Schizochytrium mangrovei* have not been classified into the Ulkenia genus, because they form amoebic irregular-shaped cells in a nutrient medium as described above but do not form the same in a sea water/pine pollen medium. On the basis of the above, it is believed that the classification of the SR21 strain into the Ulkenia genus is not suitable because it forms amoebic irregular-shaped cells in a nutrient medium but they are not observed in the medium consisting only of sea water.

On the other hand, the character in which a vegetative cell occurring after the attachment of one zoospore repeats binary fission to form a mass consisting of a number of vegetative cells and each differentiates into a zoosporangium is stable irrespective of the medium composition and is always observed in the life cycle of the SR21 strain. This character and the other characteristics observed in the SR21 strain are consistent with the description of the Schizochytrium genus reported by Goldstein et al. [Goldstein, S. and Belsky, M., Am. J. Bot., 51: 72 (1964)] and Booth et al. [Booth, T. and Miller, C. E., Can. J. Bot., 47: 2051 (1969)]. Accordingly, it can be judged that the SR21 strain is reasonably classified into the Schizochytrium genus.

At present, the following four species are described in the literature as microorganisms belonging to the Schizochytrium genus.

In *Schizochytrium aggregatum*, the vegetative cells form a cell mass in which a number of cells produced by continuous fission are attached to one another. In the cell mass, 3 to 4 or more cells differentiate into zoosporangia. Moreover, one zoosporangium forms 16 to 64 zoospores. In addition, it has been described that the release of zoospores from two cells is not observed [Goldstein, S. and Belsky, M., Am. J. Bot., 51: 72 (1964); Booth, T. and Miller, C. B., Can. J. Bot., 47: 2051 (1969)].

In *Schizochytrium minutum*, a cell mass consisting of 4 to 8 or a few hundreds of cells is formed as a result of fission of vegetative cells in a similar manner as *Schizochytrium aggregatum*, and two zoospores are released from each zoosporangium. The zoospore has a bean-like shape and two flagella are about 8.5 $\mu$m and 3.0 $\mu$m in length [Gaertner, A., Veroff. Inst. Meerestorsch. Bremer., 19: 61 (1981)].

Also, *Schizochytrium octosporum* differs from *Schizochytrium minutum* in terms of the fact that eight zoospores are released from one zoosporangium [Raghukumar, S., Trans. Br. Mycol. Soc., 90: 273 (1988)].

In addition, the microorganism belonging to the Thraustochytriidae family isolated from rotted leaves of mangrove in Goa (India) by Raghukumar in 1987 was classified into the Schizochytrium genus, due to the fact that vegetative cells form a cell mass via continuous division. However, the microorganism followed a process in which a vegetative cell divided into 4, 6, 8 or 12 cells via continuous binary fission and each cell directly became a zoospore, but the microorganism did not take the morphology of zoosporangium, in contrast to the fact that zoospores of all the above three species which had been previously described were formed in a bag called zoosporangium. Raghukumar paid attention to the feature and established a new species *Schizochytrium mangrovei* [Trans. Br. Mycol. Soc., 90: 627 (1980)].

In the same literature, Raghukumar proposed a key for the previously known microorganisms belonging to the Schizochytrium genus (Table 1).

TABLE 1

Key for four species belonging to *Schizochytrium* genus (by Raghukumar)

| | | |
|---|---|---|
| 1. | An attached zoospore forms a mass of cells via repeated binary fission and each cell differentiates into a zoosporangium | 2 |
| 1. | An attached zoospore forms a mass of cells via repeated binary fission and each cell differentiates into a zoospore | *S. mangrovei* |
| 2. | Diameter of the zoosporangium is 15 to 25 $\mu$m and the zoosporangium forms 16 to 64 zoospores | *S. aggregatum* |
| 2. | Diameter of the zoosporangium is not greater than 14 $\mu$m and the zoosporangium forms 2 or 8 zoospores | 3 |
| 3. | The zoosporangium forms 8 zoospores | *S. octosporum* |
| 3. | The zoosporangium forms 2 zoospores | *S. minutum* |

The fungological characteristics of the SR21 strain are compared with the key shown in Table 1 and the description in the original papers disclosing known four species. Firstly, the Schizochytrium genus SR21 strain differs from *Schizochytrium mangrovei* in which divided vegetative cells do not take the morphology of zoosporangium but each cell becomes a zoospore. If the diameter of zoosporangium is not greater than 14 $\mu$m and two zoospores are formed from each zoosporangium, the SR21 strain is assigned to *Schizochytrium minutum*. Similarly, if eight zoospores are formed, the strain is assigned to *Schizochytrium octosporum*. However, the SR21 strain differs from both of these species, because the zoosporangium differentiates into 8 to 16 zoospores. Furthermore, if the diameter of zoosporangium is 15 to 25 $\mu$m and the zoosporangium forms 16 to 64 zoospores (however, the original paper disclosing the species uses only the term "many"), the SR21 strain is assigned to *Schizochytrium aggregatum*. Since, however, amoebic irregular-shaped cells were not observed in this species, the SR21 strain also differs from the species. In addition, vegetative cells not going through binary fission or cells differentiating into zoospores without going through irregular-shaped cells are also observed in the SR21 strain. From the facts described above, it is recognized that the SR21 strain can not be assigned to any of the previously known four species belonging to the Schizochytrium genus, but is a new species belonging to the Schizochytrium genus.

The Schizochytrium genus SR21 strain was deposited at the National Institute of Bioscience and Human-Technology, Agency of Industrial Science and Technology in the name of "Marine fungus SR21 strain" on Mar. 6, 1995 and obtained an accession number of FERM BP-5034. Moreover, the strain was deposited at Institute of Fermentation in OSAKA (IFO) on Mar. 17, 1995 and obtained an accession number of IFO 32693.

The microorganism used in the present process for preparing a fat containing DHA and DPA is not limited to the above-mentioned FERM BP-5034 or IFO 32693, but any strain can be used for this purpose if, in the light of the above-mentioned fungological properties of the Schizochytrium genus SR21 strain, the strain is recognized as belonging to the same species as does said SR21 strain or as having substantially the same fungological properties as does said SR21 strain.

Furthermore, the microorganism used here includes wild-type, variant and recombinant strains. One of the features of the present invention lies in the recognition of the ability of a microorganism to produce a fat having special lipid properties, and the solution of the problem maintaining a stable, reliable and economical source for such a fat having high functionality and a high additional value according to the recognition. Therefore, wild-type strains producing the (n-3) series of docosahexaenoic acid and the (n-6) series of docosapentaenoic acid to a greater degree as well as variant and recombinant strains designed to produce these highly unsaturated fatty acids to a greater degree are wholly within the scope of the present invention. Such variant or recombinant microorganisms include those designed to have a higher content of the (n-3) series of docosahexaenoic acid and/or the (n-6) series of docosapentaenoic acid in a fat, a higher total amount of the fat, or both of these characteristics, in comparison with the amount produced by the original wild-type strains, when cultured using the same substrates.

In addition, microorganisms designed to produce a fat containing a similar amount of the (n-3) series of docosahexaenoic acid and the (n-6) series of docosapentaenoic acid as compared with the corresponding wild-type strains, effectively using substrates having a superior cost performance, are also included.

The microorganisms according to the present invention which can produce a fat containing the (n-3) series of docosahexaenoic acid and the (n-6) series of docosapentaenoic acid can be selected, for example, in accordance with the screening method as follows. Thus, collected sea water is filtrated using 0.4 $\mu$m pore size of a sterilizing filter to collect microorganisms, the filter is placed on an agar medium comprising 90% natural sea water, glucose, yeast extract and peptone, and cultivation is carried out at 20 to 30° C. Colonies formed on the filter put on the agar plate medium are cultured on an agar medium having the same composition as described above, and the resulting cell bodies are collected with a spatula. Fatty acids are directly methyl-esterified from the cell bodies according to a conventional method, the composition of the methyl esters is analyzed by gas chromatography, and strains which produce the (n-3) series of docosahexaenoic acid and the (n-6) series of docosapentaenoic acid are selected. It is also possible to select strains which produce fat in cell bodies in an amount of not less than 10% by weight, preferably not less than 20% by weight, per dried cell bodies and/or strains in which the content of eicosapentaenoic acid in total fatty acids is less than 1% by weight, preferably less than 0.5% by weight.

The Schizochytrium genus SR21 strain according to the present invention can produce fat in an amount of not less than 20% by weight per dried cell bodies. Moreover, the strain contains 25 to 45% by weight of the (n-3) series of docosahexaenoic acid and 6 to 11 % by weight of the (n-6) series of docosapentaenoic acid per total fatty acids in the fat, but the percent content of eicosapentaenoic acid is less than 1% by weight. In addition, the fat according to the present invention contains not less than 98% by weight of the (n-3) series of docosahexaenoic acid in the (n-3) series of fatty acids.

Accordingly, the strains lying within the scope of the present invention, which belong to the same species as does the Schizochytrium genus SR21 strain or have substantially the same fungological properties as does said strain, produce the fat preferably in an amount of not less than 10% by weight, more preferably in an amount of not less than 20% by weight, and most preferably in an amount of not less than 30% by weight, per dried cell bodies. Also, the strains contain the (n-3) series of docosahexaenoic acid preferably in an amount of not less than 15% by weight, more preferably in an amount of not less than 20% by weight, and most preferably in an amount of not less than 35% by weight, per total fatty acids in the fat. Furthermore, the strains contain the (n-6) series of docosapentaenoic acid preferably in an amount of not less than 4% by weight, more preferably in an amount of not less than 5% by weight, and most preferably in an amount of 6 to 11% by weight, per the total of fatty acids in the fat. Moreover, the percent content of eicosapentaenoic acid in the fat is preferably less than 2% by weight, more preferably less than 1% by weight, and most preferably less than 0.5% by weight. In addition, the fat according to the present invention contains not less than 90% by weight, preferably not less than 95% by weight, of the (n-3) series of docosahexaenoic acid in the (n-3) series of fatty acids, and contains the (n-3) series of docosahexaenoic acid and the (n-6) series of docosapentaenoic acid at a ratio of 3 to 6 parts by weight of the (n-3) series of docosahexaenoic acid to one part by weight of the (n-6) series of docosapentaenoic acid.

The fat according to the present invention can be obtained by inoculating a suitable medium prepared using natural or artificial sea water with the above-mentioned microorganism and by carrying out cultivation according to a conventional method.

Examples of a carbon source added to the medium are carbohydrates such as glucose, fructose, xylose, saccharose, maltose or soluble starch as well as oleic acid, fats such as soybean oil, molasses, glycerol, mannitol, and sodium acetate, but it is not limited thereto. These carbon sources may be used, for example, at a concentration of 20 to 120 g per liter of medium.

Examples of a nitrogen sources are natural nitrogen sources such as peptone, yeast extract, malt extract, meat extract, casamino acid and corn steep liquor, organic nitrogen sources such as sodium glutamate and urea, or inorganic nitrogen sources such as ammonium acetate, ammonium sulfate, ammonium chloride, ammonium nitrate and sodium sulfate, but it is not limited thereto.

Furthermore, if necessary, phosphates, such as potassium phosphate and potassium dihydrogen phosphate, inorganic salts, such as ammonium sulfate, sodium sulfate, magnesium sulfate, iron sulfate, copper sulfate, magnesium chloride and calcium chloride, and vitamins may be used as trace nutrients. The concentration of each of these components for the medium is not limited providing the concentration is not harmful to the growth of microorganisms.

After preparing the medium, the pH is adjusted to the range of between 4.0 and 6.5 using a suitable acid or base, and the medium is sterilized by autoclaving. Cultivation of the microorganisms is usually carried out for 3 to 7 days at 10 to 35° C., preferably 17 to 30° C. by aeration-agitation culture, shaking culture, stationary culture or the like.

Furthermore, in order to accelerate the production of the (n-3) series of docosahexaenoic acid and/or the (n-6) series of docosapentaenoic acid, a precursor for the (n-3) series of docosahexaenoic acid and/or the (n-6) series of docosapentaenoic acid may be added to the medium. Examples of a precursor are hydrocarbons, such as tetradecane, hexadecane and octadecane, fatty acids, such as tetradecanoic acid, hexadecanoic acid, octadecanoic acid and oleic acid, or their salts (e.g. sodium or potassium salts); fatty acid esters, or fats containing fatty acids as a constituent (e.g. olive oil, soybean oil, cottonseed oil or palm oil), but it is not limited thereto.

The following conditions are mentioned as those for producing the present fat in a yield which allows the fat to be used for commodities. Investigation of culture conditions for the Schizochytrium genus SR21 strain revealed that the SR21 strain as well as a strain belonging to the same species as does said SR21 strain or having substantially the same fungological properties as does said SR21 strain grow well in natural or artificial sea water or in a medium containing a ½ concentration of natural or artificial sea water at a pH of 3.5 to 6.0, preferably at a pH of 4.0 to 4.5.

Carbon sources and nitrogen sources added to the medium may be those conventionally used as described above. The nitrogen sources may be either organic or inorganic nitrogen sources, and the ratio of organic nitrogen sources to inorganic nitrogen sources may be varied without influencing the amount of grown cell bodies, the content of lipid or the amount of accumulated DHA and DPA, if the concentration of nitrogen is kept constant. These sources are added to the medium at the usual concentration used for cultivation of a microorganism to obtain a good growth. Also, phosphates may be used at a usual concentration used for cultivation of a microorganism to accomplish a good growth.

It is possible to carry out a high-concentration cultivation by increasing the concentration of carbon sources as well as the concentration of nitrogen sources in the medium at the same rate. In proportion to the increase rate of the carbon and nitrogen sources, the amount of dried cell bodies and the amount of lipids increase and the yield of DHA and DPA also increase.

In carrying out the high-concentration cultivation, it is possible to adopt a method in which only the concentration of the carbon sources (e.g. glucose) is increased and the nitrogen sources (e.g. corn steep liquor/ammonium sulfate) are added in the usual amount at the onset of cultivation and the amount of deficit is added at a later stage according to the amount of consumed glucose. Also, in carrying out the high-concentration cultivation, it is possible to maintain the carbon and nitrogen sources at a low concentration at the onset of cultivation, and to increase the carbon and nitrogen sources at a later stage according to the consumption of glucose.

The cultivation under the above conditions can be carried out using a conventional agitation-fermenter. It is also possible to use a bubble column fermenter. Usual culturing conditions for a microorganism may be used as conditions for aeration-agitation culture. In the aeration-agitation culture, a remarkable increase of the growth rate and the yield of cell bodies is observed, as compared with a flask culture, by raising the agitation rate to increase the amount of dissolved oxygen.

In the early stage of cultivation, it is particularly important to maintain the amount of dissolved oxygen at a high level to increase the growth rate.

By culturing as described above, it is possible to produce cell bodies, which produce a fat containing the (n-3) series of docosahexaenoic acid and the (n-6) series of docosapentaenoic acid, in a culture of high concentration of not less than 10 g, preferably not less than 20 g, more preferably not less than 40 g, per liter of medium. Furthermore, much fat accumulates in the cell bodies in or after the mid stage of cultivation, and the content of the fat can not be less than 30% by weight, preferably not less than 50% by weight, more preferably not less than 60% by weight, per dried cell bodies.

For collecting the cell bodies from the culture, a conventional method such as centrifugation or filtration can be used.

The fat containing the (n-3) series of docosahexaenoic acid and the (n-6) series of docosapentaenoic acid can be obtained by destroying the collected cell bodies, for example, using dyno-mill or ultrasonication, and then carrying out extraction with a solvent such as chloroform, hexane, methanol or ethanol. The content of the fat containing the (n-3) series of docosahexaenoic acid and the (n-6) series of docosapentaenoic acid per gram of dried cell bodies is preferably greater than about 0.3 g and more preferably greater than 0.6 g.

The present invention relates to the fat thus obtained from the Schizochytrium genus SR21 strain or a strain belonging to the same species as does said SR21 strain or having substantially the same fungological properties as does said SR21 strain. Lipid properties of the fat are usually as follows. The percentage of neutral lipids is very high and constitutes not less than 90% by weight of total lipids. The composition of fatty acids in the neutral lipids is as follows: 45 to 55% by weight of palmitic acid, 30 to 40% by weight of the (n-3) series of docosahexaenoic acid, 5 to 10% by weight of the (n-6) series of docosapentaenoic acid, 0 to 1% by weight of the (n-3) series of eicosapentaenoic acid, 0 to 0.6% by weight of arachidonic acid, and about 10 to 20% by weight of the other fatty acids. In this case, the ratio of DHA to DPA is 3 to 6 parts by weight of DHA to one part by weight of DPA.

More than about 85%. by weight, preferably more than 90% by weight of the resulting neutral lipids is triglycerides, and they contain few diglycerides and monoglycerides. The lipids also contain 2 to 3% of free sterols and sterol esters. The molecular species of triglycerides in the fat having the above fatty acid composition are mainly as follows: 14:0—16:0—16:0, 16:0—16:0—16:0, 14:0—16:0—22:6, 16:0—16:0—22:5, 16:0—16:0—22:6, 16:0—22:5—22:6 and 16:0—22:6—22:6 (bonding positions of fatty acid residues are not defined). In the above expression "14:0", "14" shows the number of carbon atoms in the fatty acid and "0" shows the number of double bonds in the fatty acid. For example, the expression "16:0" shows a fatty acid having 16 carbon atoms and not having any double bond.

Moreover, the triglycerides include those wherein the (n-3) DHA is only attached to the 2-position of glycerin, or those wherein the (n-3) DHA is attached to the 1- and 2-positions or the 1- and 3-positions of glycerin.

The polar lipids are mostly constituted by phosphatidyl choline, and the lipids contain phosphatidyl ethanolamine, phosphatidyl inositol and the like as other components.

Separation of the (n-3) series of docosahexaenoic acid or the (n-6) series of docosapentaenoic acid from a fat containing the (n-3) series of docosahexaenoic acid and the (n-6) series of docosapentaenoic acid is carried out by converting the fat into mixed fatty acids or fatty acid esters, and then concentrating and separating them, using a conventional method, such as urea-addition, cooling-separation or column chromatography. In addition, separation of the triglycerides containing the (n-3) series of docosahexaenoic acid and/or the (n-6) series of docosapentaenoic acid from the fat collected from cultured cell bodies or the like is carried out by a conventional method, such as cooling-separation or column chromatography. When using the Schizochytrium genus SR21 strain according to the present invention, concentration and separation of the (n-3) series of docosahexaenoic acid and the (n-6) series of docosapentaenoic acid can easily be carried out because arachidonic acid or EPA is hardly contained as an unsaturated fatty acid. Accordingly, use of the strain is advantageous for a high-concentration production.

The fat according to the present invention can be utilized as a source of the (n-3) DHA and/or (n-6) DPA for various products, such as feedstuffs or foods. When utilizing the present fat for the products, it is possible to use the fat collected from cultured cell bodies or the (n-3) DHA and/or (n-6) DPA obtained by purifying the fat. However, it is also possible to use, for example, a culture or a sterilized culture in the course of producing the fat by cultivation of a microorganism, or a culture or a sterilized culture at the end of cultivation, or cultured cell bodies collected from any culture or dried cell bodies, or residues obtained after recovering the fat from any culture or cell bodies.

Also, the present invention relates to a feedstuff for animals to which the fat according to the invention is added. Examples of the present feedstuff for animals are pet foods such as dog foods, cat foods and the like, feed for domestic fowl such as chickens, feed for domestic animals, such as pigs or cows, or feed for fish breeding. Cell bodies or cultured cells of a microorganism according to the present invention, which produced and accumulated a fat containing the (n-3) DHA and (n-6) DPA, are preferable because oxidation of the fat is prevented and the fat is stable against sterilization by heating, due to protection of the fat in the cell bodies. It is also possible to use residues obtained after extracting a fat containing the (n-3) DHA and (n-6) DPA from cultured cell bodies of a microorganism for the present feedstuff for animals. The residues obtained after the extraction are preferable because they also contain proteins, ash contents and carbohydrates in addition to the (n-3) DHA and (n-6) DPA.

Moreover, the present invention relates to a bait for bait-microorganisms comprising cultured media or cultured cell bodies in which the present fat is produced and accumulated. In culturing fish and shellfish, bait-microorganisms (zooplanktons such as Shiomizu-tsubo-wamushi (a species of Rotifera) or brine shrimp) are hitherto used for the production of seeds (fry) and it is therefore necessary to culture these bait-microorganisms in advance of culturing the fry. When culturing these bait-microorganisms, the bait given to the bait-microorganisms is determined in view of the nutrient requirement of the fry which subsequently take the bait-microorganisms as a bait. The bait-microorganisms, which contain the (n-3) DHA and (n-6) DPA and can satisfy the nutrient requirement of the fry, are obtained by giving the cultured media or the cultured cell bodies containing the present fat to the bait-microorganisms.

The present invention further includes a bait for fish and shellfish which contains the above bait-microorganisms.

Also, the present invention relates to the use of the present fat in the production of eggs from domestic fowl which are enhanced with the (n-3) DHA and/or (n-6) DPA as well as in the production of a yolk oil which is enhanced with the (n-3) DHA and/or (n-6) DPA. The present eggs of domestic fowl which are enhanced with the (n-3) DHA and/or (n-6) DPA are produced by giving the above feedstuff for animals to the domestic fowl for taking eggs (in particular, to hens) and breeding the fowl. The present yolk oil which is enhanced with the (n-3) DHA and/or (n-6) DPA is obtained by extracting a fat from such eggs of domestic fowl (in particular, from yolk) according to a conventional method. In addition, the present invention also relates to the use of the yolk oil as an additive in milk preparations for babies, milk preparations for premature babies, foods for children, or foods for pregnant women and nursing mothers.

Furthermore, the present invention relates to milk preparations for babies, milk preparations for premature babies, foods for children, and foods for pregnant women and nursing mothers which contain the fat according to the present invention. As to a powder milk for nursing, in particular, attempts to allow its components to resemble those of human milk as much as possible have been made for a long time, and it has become an important problem to prepare the powder milk so that each component in the powder milk resembles that in the human milk, particularly each of the components such as proteins, fats and sugars which constitute the major components in human milk. For the fats, in particular, it has become problematic that traditional powder milk for nursing lacks the highly unsaturated fatty acids naturally contained in human milk. In this context, there are various reports as to the composition of unsaturated fatty acids in human milk. For example, "INFORM" [Vol. 6, No. 8, pp. 940–946 (August, 1995)] discloses the composition of highly unsaturated fatty acids in the human milk of American, European and African women, and "JJPEN" [Vol. 13, No. 9, pp. 765–772 (1991)] discloses the composition of highly unsaturated fatty acids in the human milk of Japanese women.

Recently, it has been reported that arachidonic acid and DHA are similarly contained in human milk and are useful for babies' growth ["Advances in Polyunsaturated Fatty Acid Research", Elsevier Science Publishers, pp.261–264 (1993)]. In addition, it has been reported that the acids have an importance in the development in the brain or stature of fetuses [Proc. Natl. Acad. Sci. USA, 90: 1073–1077 (1993); Lancet, 344: 1319–1322 (1994)].

Accordingly, there is a trend toward the addition of arachidonic acid and DHA to powder milk preparations, these acids constituting a great difference in the fatty acid composition between human milk and powder milk preparations. Thus, a powder milk preparation to which fish oil is added for the purpose of adding DHA to the preparation is marketed, but essentially, human milk hardly contains any EPA which is contained in the fish oil. It has become apparent from a recent study that EPA is disadvantageous to the growth of premature babies ["Advances in Polyunsaturated Fatty Acid Research", Elsevier Science Publishers, pp.261–264 (1993)]. U.S. Pat. No. 5,374,657 discloses a fat for adding to milk preparations for children, the fat being prepared by combining a cooking oil comprising arachidonic acid-containing cells and a cooking oil comprising DHA-containing cells poor in EPA. However, it was not previously known at all that a fat containing the (n-3) DHA and (n-6) DPA essentially contained in human milk is used in a milk preparation or a fat for adding to the milk preparation known until then.

The fat according to the present invention, which is derived from the Schizochytrium genus SR21 strain or a strain belonging to the same species as does said SR21 strain or having substantially the same fungological properties as does said SR21 strain, contains 3 to 6 parts by weight of the (n-3) DHA per one part by weight of the (n-6) DPA and hardly contains any EPA, and not less than 85% of the fat is triglycerides, and therefore, the fat is suitable for preparing a milk preparation for nursing which resembles human milk.

Moreover, the present invention relates to foods such as foods for supplementing nutrients, foods for the old or foods for health to which the fat according to the present invention is added. The foods according to the present invention are intended to supplement the (n-3) DHA and/or (n-6) DPA and are used for maintenance of health or the like. The form of the foods may be either solid or liquid foods or luxury foods. Examples of foods containing the fat are as follows; natural foods such as meat, fish or nuts, foods to which a fat is added when cooking such as Chinese dishes, Chinese noodles or soup, foods in which a fat is used as a thermal medium such as tempura (Japanese fried food), fry, fried bean curd, Chinese dishes of fried rice, doughnuts or fried dough cakes, fatty foods or processed foods to which a fat is added when processing such as butter, margarine, mayonnaise, dressing, chocolate, precooked Chinese noodles, caramels, biscuits, cookies, cakes or ice creams, and foods to which a fat is sprayed or applied when processing and finishing such as rice crackers, hard biscuits or bean-jam buns. However, the foods according to the present invention are not limited to those containing the fat, but bread, noodles, boiled rice, confectionery (candies, chewing gums, gummy candies, tablets or Japanese-style confections), agricultural foods, such as bean curd; and foods obtained by processing the curd, fermentative foods, such as sake, medicinal alcoholic drink, sweet sake, vinegar, soy sauce or miso; farm foods, such as yogurt, ham, bacon or sausage; marine foods, such as boiled fish paste, fried fish paste or fish cake, drinks, such as fruit drinks, refreshing drinks, sports drinks, alcoholic drinks or tea; and the like can be mentioned, for example.

The foods according to the present invention can be processed and prepared conventionally by formulating a predetermined amount of the present fat together with food sources. The amount of the fat added is not limited and varies according to the form of the formulation or the form and property of the foods. In general, the amount is preferably from 0.001 to 50% by weight per total amount of food.

Furthermore, the present invention relates to functional foods (including special foods for health) to which the fat according to the present invention is added. The functional foods according to the present invention are intended to perform the physiological activities possessed by the (n-3) DHA and/or (n-6) DPA. Thus, they are foods for recuperating a healthy state from a state in which a function is depressed and for maintaining the former state or for preventing the depression of the function. Although they may be in the form of a pharmaceutical formulation, they may be in processed forms such as natural fluid foods, semi-digested nutritious foods and componential nutritious foods as well as drink formulations and transintestinal nutritious formulations which are prepared by adding the present fat to proteins (proteins such as milk proteins, soybean proteins or ovalbumin, which have a high trophic value and a good amino acid balance, are most widely used as protein sources, although degradation products of these proteins, egg white oligopeptides, soybean hydrolysates and the like may be also used in addition to a mixture of amino acids), sugars, fats, trace elements, vitamins, emulsifiers, flavorings and the like. Also, they may be in the form of the foods and drinks as mentioned above.

The functional foods and the foods for supplementing nutrients according to the present invention can be prepared, using the present fat, as foods and drinks having a form such as a powder, granule, tablet, capsule, troche, internal solution, suspension, emulsion, syrup, drink, natural fluid food, semi-digested nutritious food, componential nutritious food or transintestinal nutritious formulation. In this case, it is possible to add any nutritious components or functional components together with the present fat to the foods and drinks. Furthermore, it is also possible to give hospital meals to a patient having the (n-3) DHA and/or (n-6) DPA lowered, which meals are prepared in situ by adding the present fat to any foods when cooking the hospital meals under the control of a dietitian following the instructions of a physician.

Also, the present invention relates to use of the present fat for preparing a pharmaceutical agent. Thus, it relates to the preparation of the (n-3) DHA or (n-6) DPA or derivatives thereof using the present fat as a starting material. The (n-3) DHA or (n-6) DPA or their mixture may be in a free form, or in the form of pharmaceutically acceptable salts, for example, sodium salt, potassium salt, lithium salt or other alkali metal salts or other metal salts, such as zinc salt, calcium salt or magnesium salt, or may be in various forms, such as monoglycerides, diglycerides, triglycerides, esters with lower alcohols, phospholipids, glycolipids or amides. In this context, the lower alcohol refers to a monohydric alcohol having 6 or less carbon atoms, and can be exemplified by methanol, ethanol, propanol, isopropanol, butanol, pentanol, hexanol or the like.

Moreover, the present invention relates to cosmetics containing the present fat. The present cosmetics can be prepared by adding the present fat to bases in various forms known for usual cosmetics, according to a conventional method. The forms of the cosmetics are not limited to particular ones, and can be exemplified by the forms of emulsion, cream, lotion, pack, dispersion, detergent or the like. The bases corresponding to the forms of cosmetics, for example, purified water, lower alcohols, polyhydric alcohols, fats, surfactants, various beauty components, ultraviolet absorbents, thickeners, pigments, preservatives, perfumes or the like can be used as the bases of the cosmetics.

Furthermore, the present invention relates to a detergent containing the present fat. The present detergent includes, for example, soaps, shampoos, facial creams, rinses and also agents for bathing which are commonly used for keeping bodies clean, whether they are applied to a medicinal or non-medicinal purpose. Also, the detergent may be that for utensils or the like used daily in the home such as tableware.

EXAMPLES

The present invention is further illustrated by the following examples but is not limited thereto.

Example 1

Production of Fat Using the Schizochytrium Genus SR21 Strain (1)

A medium was prepared by charging 1 L of 50% concentration of artificial sea water (trophic marine) into a flask and then adding a carbon source (glucose or glycerol) and a nitrogen source (corn steep liquor; hereinafter, also abbreviated to "CSL") in the amount shown in Table 2. The medium was inoculated with the Schizochytrium genus SR21 strain and shaking culture was carried out at 26° C. for 5 days.

Next, 2 ml portion of the resulting culture was taken and cell bodies were collected by centrifugation. The cell bodies were washed and dried in an oven at 110° C. for 5 hours to obtain dried cell bodies. The dried cell bodies were weighed to determine the amount of cell bodies per liter of medium. The results are shown in Table 2.

Extraction of the fat and preparation of fatty acid methyl esters were then carried out directly from the dried cell bodies according to a conventional method. Then, the dried cell bodies were charged into a test tube with a screw inlet, 10% methanolic HCl and dichloromethane were added to the tube, and the mixture reacted on heating in a water bath at 60° C. for 3 hours. The fatty acid methyl ester components were then extracted with hexane, and the fatty acid composition of the fatty acid methyl ester components was measured by gas chromatography analysis to determine the percent content of docosahexaenoic acid (DHA). Also, the total amount of fatty acids contained in the cell bodies was determined from the amount of fatty acid methyl esters detected by the gas chromatography analysis and the amount of DHA formed was determined from the amount of docosahexaenoic acid methyl ester detected, by an internal standard method in which a known amount of a internal standard substance was added in the above reaction. The total amount of fatty acids per liter of medium, the percent content of fatty acids per dried cell bodies, the percent content of DHA in total fatty acids, and the amount of DHA per liter of medium were determined as described above. These results are shown in Table 2.

In this case, DHA was confirmed by comparing it with the standard substance by gas chromatograph-mass spectrograph (GC/MS) method.

Even if the amount of the carbon source per liter of medium was high, in the order of 60 to 120 g, the cell bodies proliferated well and 21.9–35.9 g/L of cell bodies were obtained. Also, it was indicated that the amount of fatty acids per liter of medium was 8.2–14.6 g and the DHA-containing fatty acids were accumulated in a content of 30.3–58.0% by weight per dried cell bodies. In addition, it was indicated that the content of DHA in total fatty acids was high, in the order of 25.5–29.7% by weight, and the yield of DHA per liter of medium was high, in the order of 2.43–4.20 g.

Example 2

Production of Fat Using the Schizochytrium Genus SR21 Strain (2)

A medium was prepared by charging 1 L of 50% concentration of artificial sea water, 60 g of glucose as a carbon source, 4.0 g of potassium dihydrogen phosphate, 1.0 g of yeast extract and 1.0 g of corn steep liquor as an organic nitrogen source into a flask, and also adding ammonium nitrate as an inorganic nitrogen source in the amount shown in Table 3. The medium was inoculated with the Schizochytrium genus SR21 strain and shaking culture was carried out at 25° C. for 4 days.

After the cultivation, the amount of cell bodies per liter of medium, the total amount of fatty acids per liter of medium, the percent content of fatty acids per dried cell bodies, the percent content of DHA in total fatty acids, and the amount of DHA per liter of medium were determined in a similar manner to that described in Example 1. These results are shown in Table 3.

TABLE 2

| Exp. No. | Carbon source | Amount of carbon source added (g) | Amount of CSL added (g) | Amount of cell bodies (g) *1) | Total amount of fatty acids (g) *1) | Percent content of fatty acids (wt %) *2) | Percent content of DHA (wt %) *3) | Amount of DHA (g) *1) |
|---|---|---|---|---|---|---|---|---|
| 101 | Glucose | 60 | 10 | 24.2 | 14.1 | 58.0 | 26.8 | 3.77 |
| 102 | Glucose | 90 | 10 | 28.0 | 13.2 | 47.0 | 25.7 | 3.38 |
| 103 | Glucose | 120 | 10 | 27.7 | 10.5 | 37.7 | 29.0 | 3.03 |
| 104 | Glucose | 60 | 20 | 26.9 | 8.2 | 30.3 | 29.7 | 2.43 |
| 105 | Glucose | 90 | 20 | 35.9 | 14.1 | 39.3 | 29.7 | 4.20 |
| 106 | Glycerol | 60 | 10 | 24.2 | 12.9 | 53.2 | 26.8 | 3.45 |
| 107 | Glycerol | 90 | 10 | 21.9 | 11.9 | 54.3 | 25.5 | 3.04 |
| 108 | Glycerol | 60 | 20 | 28.3 | 11.3 | 39.9 | 28.0 | 3.16 |
| 109 | Glycerol | 90 | 20 | 35.4 | 13.9 | 39.3 | 26.5 | 3.68 |
| 110 | Glycerol | 120 | 20 | 35.6 | 14.6 | 41.0 | 28.4 | 4.15 |

*1) Amount per liter of medium
*2) Percentage per dried cell bodies
*3) Percentage per total fatty acids

TABLE 3

| Exp. No. | Nitrogen source | Amount of nitrogen source added (g) | Amount of cell bodies (g) *1) | Total amount of fatty acids (g) *1) | Percent content of fatty acids (wt %) *2) | Percent content of DHA (wt %) *3) | Amount of DHA (g) *1) |
|---|---|---|---|---|---|---|---|
| 201 | Ammonium nitrate | 0.6 | 14.6 | 7.6 | 51.8 | 30.7 | 2.32 |

TABLE 3-continued

| Exp. No. | Nitrogen source | Amount of nitrogen source added (g) | Amount of cell bodies (g) *1) | Total amount of fatty acids (g) *1) | Percent content of fatty acids (wt %) *2) | Percent content of DHA (wt %) *3) | Amount of DHA (g) *1) |
|---|---|---|---|---|---|---|---|
| 202 | Ammonium nitrate | 1.0 | 19.2 | 7.4 | 38.8 | 30.0 | 2.24 |
| 203 | Ammonium acetate | 0.7 | 17.8 | 8.1 | 45.3 | 29.1 | 2.35 |
| 204 | Ammonium acetate | 1.2 | 23.0 | 9.2 | 40.1 | 32.9 | 3.03 |

*1) Amount per liter of medium
*2) Percentage per dried cell bodies
*3) Percentage per total fatty acids From these results, it was found that the SR21 strain can rate well even if the inorganic nitrogen is used as a nitrogen and that the SR21 strain produces DHA efficiently.

Example 3

Production of Fat Using the Schizochytrium Genus SR21 Strain (3)

Cultivation was carried out in a jar fermenter (fermenter volume: 5 L, amount of medium: 3 L), using the medium (A) composed of 60 g of glucose, 20 g of polypeptone, 10 g of yeast extract and 1 L of 50% concentration of artificial sea water or the medium (B) composed of 90 g of glucose, 10 g of polypeptone, 10 g of corn steep liquor and 1 L of 50% concentration of artificial sea water. The cultivation was carried but at the culturing temperature of 25° C., at the aeration rate of 0.5 vvm, and at the agitation rate of 200 rpm.

After the cultivation, the cell bodies were collected by centrifugation and freeze-dried, and the amount of cell bodies per liter of medium was determined by weighing. The results are shown in Table 4.

Next, destruction of the cell bodies and extraction of a fat were carried out by adding a chloroform/methanol (2:1: v/v) mixture to the dried cell bodies and homogenizing the resulting mixture in the presence of glass beads. After the extract was washed by the Folch method, the solvent was evaporated off to obtain a purified fat and the fat was weighed. Using a portion of the resulting fat, fatty acid methyl esters were prepared conventionally, and the amount of the fat and the percent content of DHA in the total fat were determined by gas chromatography. The amount of DHA formed was calculated by multiplying the amount of the fat formed by the percent content of DHA. These results are shown in Table 4.

TABLE 4

| Exp. No. | Medium | Culturing time (days) | Amount of cell bodies (g) *1) | Total amount of fat (g) *1) | Percent content of fat (wt %) *2) | Percent content of DHA (wt %) *3) | Amount of DHA (g) *1) |
|---|---|---|---|---|---|---|---|
| 301 | (A) | 7 | 35.0 | 8.7 | 24.8 | 43.7 | 3.8 |
| 302 | (B) | 14 | 39.6 | 21.2 | 53.5 | 34.0 | 7.2 |

*1) Amount per liter of medium
*2) Percentage per dried cell bodies
*3) Percentage per total fatty acids In addition, the fatty acid composition of the DHA-containing fat was analyzed by gas chromatography, the results being shown in the following Table 5.

TABLE 5

| Exp. No. | Fatty acid composition (% by weight) | | | | | | | | |
|---|---|---|---|---|---|---|---|---|---|
| | 14:0 | 15:0 | 16:0 | 17:0 | 18:0 | 20:4 (AA) | 20:5 (EPA) | 22:5 (DPA) | 22:6 (DHA) |
| 301 | 1.6 | 10.1 | 25.0 | 1.8 | 1.0 | — | 0.4 | 11.1 | 43.7 |
| 302 | 2.8 | 6.7 | 44.6 | 1.6 | 1.3 | — | 0.4 | 8.5 | 34.0 |

From the above results, it was found that the Schizochytrium genus SR21 strain well proliferates even in an aeration-agitation culture which is a practical culturing method, and also the strain effectively produces a fat having a high DHA content. The yield of DHA reaches 7.2 g per liter of medium at maximum, and therefore, the productivity is extremely excellent.

From Table 5, it was also found that, as a highly unsaturated fatty acid, docosahexaenoic acid (DHA) is contained in an extremely high concentration and docosapentaenoic acid (DPA) is also contained, but little arachidonic acid (AA) or eicosapentaenoic acid (EPA) is contained. Accordingly, it was shown that concentration and separation procedures of DHA are easy as compared with fish oil which contains the latter fatty acids in an amount of around 10% by weight.

Example 4

The percent content of each of the (n-3) series of fatty acids such as docosahexaenoic acid (DHA) and eicosapentaenoic acid (EPA) which are contained in the fats obtained in Examples 1 to 3 as well as the percentage of DHA in a total amount of the (n-3) series of fatty acids are shown in Table 6.

TABLE 6

(n − 3) Fatty acid composition (% by weight)

| Exp. No. | EPA | DPA | DHA | Percentage of DHA per total (n − 3) fatty acids |
|---|---|---|---|---|
| 101 | 0.3 | 0.1 | 26.8 | 98.5 |
| 102 | 0.2 | Tr  | 25.7 | 99.2 |
| 103 | 0.2 | 0.1 | 29.0 | 98.9 |
| 104 | 0.1 | 0.1 | 29.7 | 99.5 |
| 105 | 0.3 | Tr  | 29.7 | 98.9 |
| 106 | 0.3 | 0.1 | 26.8 | 98.7 |
| 107 | 0.1 | 0.1 | 25.5 | 99.2 |
| 108 | 0.3 | 0.1 | 28.0 | 98.5 |
| 109 | 0.1 | 0.1 | 26.5 | 99.4 |
| 110 | 0.3 | 0.1 | 28.4 | 98.8 |
| 201 | 0.3 | 0.1 | 30.7 | 98.7 |
| 202 | 0.5 | 0.1 | 30.0 | 98.0 |
| 203 | 0.2 | 0.1 | 29.1 | 99.0 |
| 204 | 0.2 | 0.2 | 32.9 | 98.8 |
| 301 | 0.4 | 0.2 | 43.7 | 98.6 |
| 302 | 0.4 | 0.1 | 34.0 | 98.6 |

Tr: less than 0.05% by weight

In the DHA-containing fat obtained from the Schizochytrium genus SR21 strain, the percent content of EPA which is largely contained in fish oil is 1.0% by weight or less, and the percent content of DHA in a total amount of the (n-3) series of fatty acids is 98% by weight or more. These facts show that the strain has the advantages of providing simple procedures for concentrating, separating and purifying DHA, as compared with fish oil which contains EPA in an amount of around 10% by weight.

Reference Example

Comparison with Known Microorganisms

The ability of the Schizochytrium genus SR21 strain according to the present invention to produce DHA was compared with that of known microorganisms.

The amount of cell bodies per liter of medium, the percent content of fats or fatty acids per dried cell bodies, the percent content of DHA in total fatty acids, and the amount of DHA per liter of medium are shown in Table 7, these results being obtained when DHA is produced by cultivation of *Thraustochytrium aureum* (ATCC 34304) as a microorganism [referring to Bajapai, P., Bajapai, P. K. and Ward, O. P., Appl. Microbiol. Biotechnol. 35:706 (1991); Kendric, A. and Ratledge, C., Lipids 27:15 (1992); and Bajapai, P. K., Bajapai, P. and Ward, O. P., J. Am. Oil Chem. Soc., 68:509 (1994)], when DHA is produced by cultivation of *Japonochytrium sp.* (ATCC 28207) as a microorganism [referring to Japanese Patent Publication (Kokai) No; 199588/1989], and when DHA is produced by cultivation of *Schizochytrium aggregatum* (ATCC 28209) as a microorganism [Kendric, A. and Ratledge, C., Lipids 27:15 (1992)], as well as when DHA is produced by cultivation of the Schizochytrium genus SR21 strain according to the present invention (the above experiments Nos. 105, 204 and 302).

TABLE 7

Comparison of ability to produce DHA with those of known microorganisms

| Microorganism | Ref. or Exp. No. | Amount of cell bodies (g) *1) | Percent content of fat or fatty acids (wt %) *2) | Percent content of DHA (wt %) *3) | Percent content of EPA (wt %) *3) | Amount of DHA (mg) *1) |
|---|---|---|---|---|---|---|
| *Japonochytrium sp.* (ATCC 28207) | (a) | 1.7 | 8.2 | 30.0 | 6.4 | 42 |
| *Thraustochytrium aureum* (ATCC 34304) | (b) | 5.0 | 20.2 | 51.0 | no data | 511 |
|  | (c) | 3.8 | 16.5 | 48.5 | 3.6 | 270 |
|  | (d) | 4.0 | 10.0 | 24.1 | 9.3 | 96 |
| *Schizochytrium aggregatum* (ATCC 28209) | (d) | 1.4 | 1.7 | 6.0 | 6.1 | 1 |
| *Schizochytrium sp.* SR21 strain | No. 105 | 35.9 | 39.3 | 29.7 | 0.3 | 4200 |
|  | No. 204 | 23.0 | 40.1 | 32.9 | 0.2 | 3030 |
|  | No. 302 | 39.6 | 53.5 | 34.0 | 0.4 | 7200 |

*1) Amount per liter of medium
*2) Percentage per dried cell bodies (SR21 strain: Percentage of fatty acids; Other strains: Percentage of fat)
*3) Percentage per total fatty acids
(a) Japanese Patent Publication (Kokai) No. 199588/1989
(b) P. K. Bajapai, P. Bajapai and O. P. Ward, J. Am. Oil Chem. Soc., 68:509 (1991)
(c) P. Bajapai, P. K. Bajapai and O. P. Ward, Appl. Microbiol. Biotechnol. 35:706 (1991)
(d) A. Kendric and C. Ratledge, Lipids 27:15 (1992)

As shown in Table 7, it is apparent that, when cultivation is carried out using the Schizochytrium genus SR21 strain according to the present invention, the amount of cell bodies per medium is very high as compared with the results of known microorganisms and the SR21 strain is superior to the proliferation property. Also, the Schizochytrium genus SR21 strain according to the present invention has a very high percent content of the fat as compared with the results of known microorganisms. In addition, according to the present invention, the percent content of DHA in total fatty acids is high, in the order of 30% by weight, and, therefore, the amount of DHA per liter of medium is higher, in the order of 10 to 100 times, than that obtained using hitherto known microorganisms. Thus, it is apparent that the SR21 strain has the ability to produce DHA very well. Moreover, it can be seen that a fat having the percent content of EPA of a few percent by weight is obtained when using the known microorganisms while a fat having a very low percent content of EPA, in the order of 0.5% by weight or less is obtained when using the Schizochytrium genus SR21 strain.

Example 5

Production of Fat Using the Schizochytrium Genus SR21 Strain (4)

Cultivation was carried out for about 60 hours in a jar fermenter (fermenter volume: 5 L, amount of medium: 3 L) using a medium composed of 60 g/L of glucose, 0.5 g/L of corn steep liquor, 3 g/L of potassium phosphate, 2 g/L of ammonium sulfate and 50% concentration of artificial sea water. The cultivation was carried out under the following conditions: culturing temperature of 28° C., aeration rate of 1.0 vvm, agitation rate of 300 rpm, and control of the pH of the medium to 4 with 10% sodium hydroxide.

After cultivation, the cell bodies were collected by centrifugation, freeze-dried, and then weighed to obtain about 20 g of dried cell bodies per liter of medium.

Extraction of the fat was carried out conventionally by adding a chloroform/methanol (2:1: v/v) mixture to the dried cell bodies and homogenizing the mixture in the presence of glass beads. The weight of the crude fat extracted from 60 g of the dried cell bodies was 36 g. The crude fat was methyl-esterified according to a conventional method, and the fatty acid composition was determined by gas chromatography, which revealed the composition to be that shown in Table 8.

TABLE 8

Fatty acid composition in crude fat extracted

| Fatty acid | 14:0 | 15:0 | 16:0 | 17:0 | 18:0 | 20:4 AA | 20:5 EPA | 22:5 n − 6 DPA | 22:6 n − 3 DHA |
|---|---|---|---|---|---|---|---|---|---|
| Content (%) | 2.3 | 5.8 | 44.6 | 2.0 | 1.4 | 0.6 | 0.8 | 8.4 | 34.0 |

Example 6

Isolation and Identification of Docosapentaenoic Acid

In order to increase the concentration of highly unsaturated fatty acids in the crude fatty acids extracted, urea-addition was carried out to remove saturated fatty acids according to a conventional method. Then, 20 g of urea and 200 ml of methanol were added to about 9 g of the crude fatty acids prepared by the method as shown in Example 5, and the mixture was heated to 60° C. for 3 hours and then cooled to 10° C. gradually. Urea crystals precipitated were filtered off and the filtrate without the crystals was then concentrated to obtain about 4 g of the non-urea-addition product. The fatty acid composition of the non-urea-addition product was as follows: docosapentaenoic acid was 17.7%; docosahexaenoic acid was 77.9%, and the percent content of the other fatty acids was 5% or less.

The non-urea-addition product obtained by the above procedure was subjected to liquid chromatography (ODS column, mobile phase: acetonitrile:water=97.5:2.5, detection: UV) to separate docosapentaenoic acid, from which about 3.2 g of docosapentaenoic acid having a purity of 99% or more was obtained.

Figure 4:
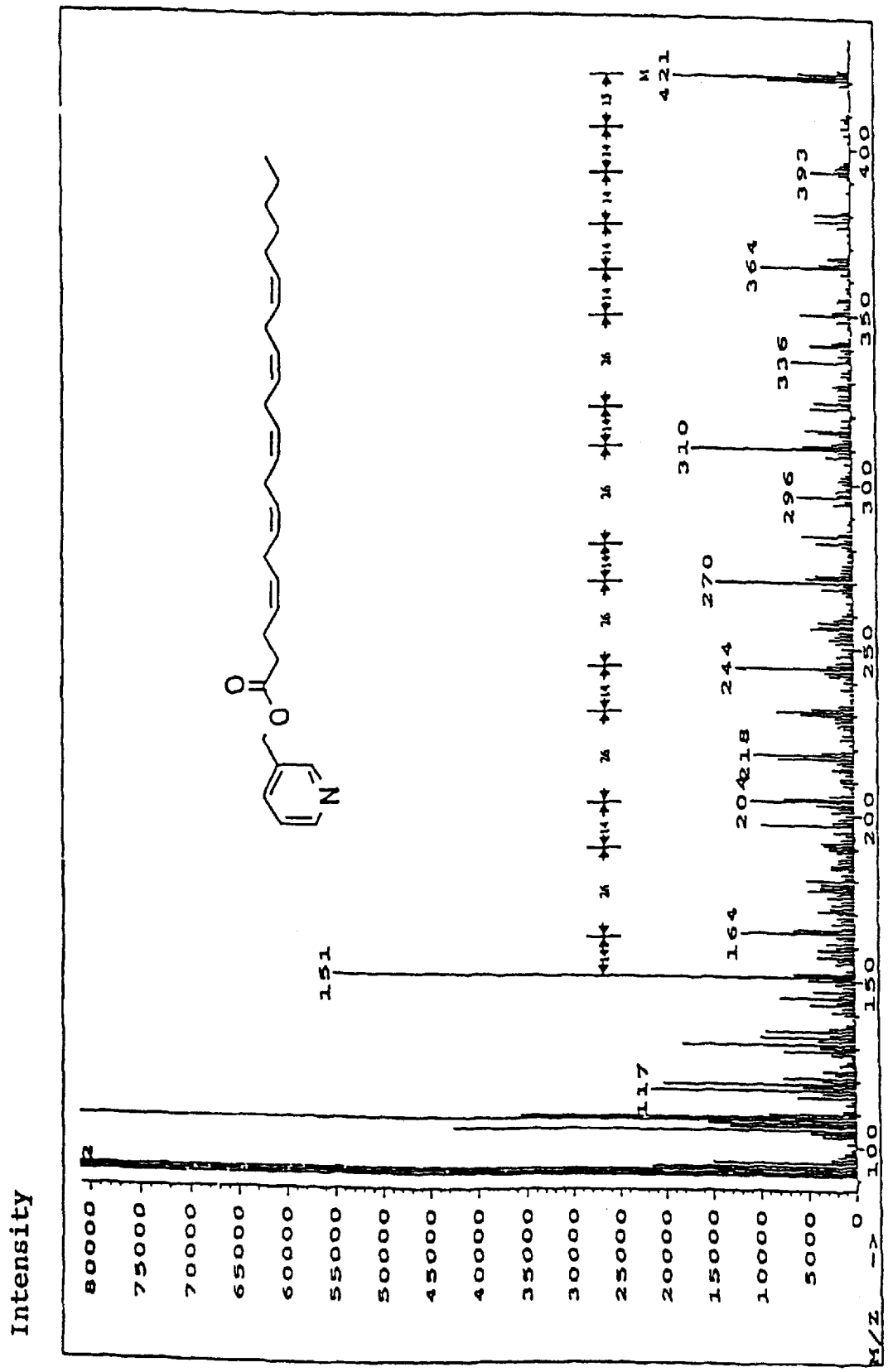
FIG. 4 is a chart showing the results obtained by measuring GC/MS spectra of the (n-6) series of docosapentaenoic acid derived from the Schizochytrium genus SR21 strain.

Furthermore, in order to determine the position of double bonds in docosapentaenoic acid, the fatty acid was converted into a piconyl ester derivative according to a conventional method, which derivative was then analyzed by GC/MS. Then, 100 μl of thionyl chloride was added to 20 μg of the non-urea-addition fatty acid obtained as described above, and the mixture was allowed to stand for one minute at room temperature and then dried under a nitrogen stream. Then, 10 μl of 10% 3-pyridylcarbonyl was added to the dried mixture, and the mixture was allowed to stand for one minute at room temperature and then analyzed by GC/MS. The result is shown in FIG. 4 and it was identified that docosapentaenoic acid (22:5) produced by the SR21 strain is an unsaturated fatty acid of the (n-6) series having unsaturated bonds at Δ4, 7, 10, 13 and 16 positions.

Example 7

Analysis of Fatty Acids Derived from the Schizochytrium Genus SR21 Strain

The crude fat extracted in Example 5 was used for the analysis. According to a conventional method, the crude fat was subjected to liquid/liquid distribution with hexane and 90% methanol to divide into neutral lipids and polar lipids. The polar lipids and the neutral lipids were obtained in the amounts of 1.8 g and 32.9 g, respectively. After the lipids were hydrolyzed, the resultant was methyl-esterified and the fatty acid composition was analyzed by gas chromatography.

The results of the analysis are as follows.

TABLE 9

Polar/neutral lipid composition in crude fat extracted

|  | Polar lipid (%) | Neutral lipid (%) |
|---|---|---|
| 14:0 | 1.3 | 3.2 |
| 15:0 | 0.6 | 1.0 |
| 16:0 | 32.4 | 49.2 |
| 20:4(n − 6) | 0.2 | 0.6 |
| 20:5(n − 3) | 0.6 | 0.8 |
| 22:5(n − 6) | 10.6 | 7.9 |
| 22:6(n − 3) | 52.1 | 33.7 |

Example 8

Analysis of Lipids Derived from the Schizochytrium Genus SR21 Strain

The neutral lipids and the polar lipids obtained in Example 7 were analyzed by thin layer chromatography according to a conventional method. The color development was performed using sulfuric acid and the identification of the resulting spots was carried out using Rf values relative to various standard lipids. It was found that 90% or more of the neutral lipids was triglycerides. It was also found that the polar lipids were mostly phosphatidylcholine and followed by phosphatidylethanolamine and phosphatidylinositol.

Figure 5:
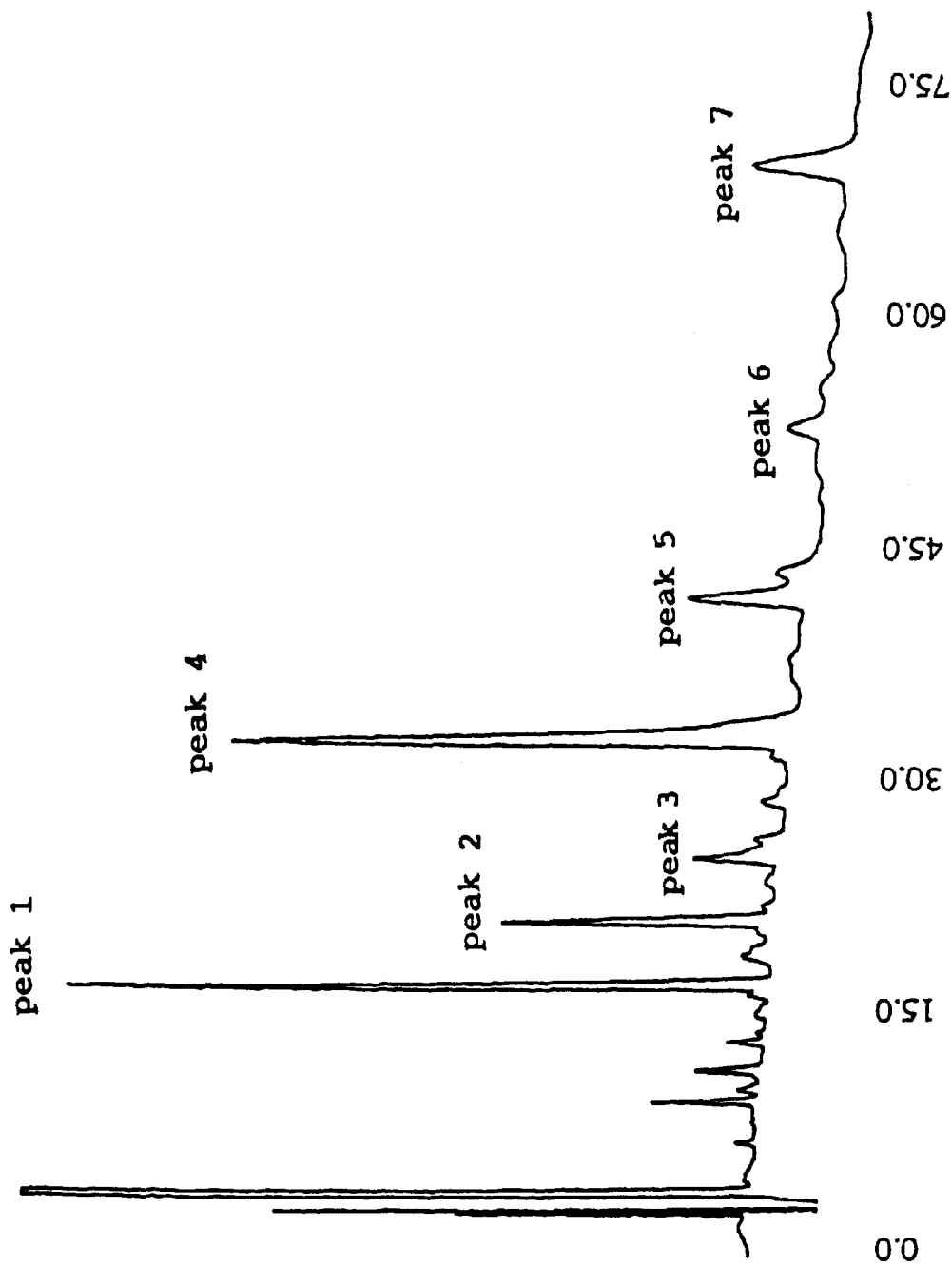
FIG. 5 is a chart showing the results obtained by separating triglycerides in the neutral fat derived from the Schizochytrium genus SR21 strain by liquid chromatography.

In addition, the triglycerides contained in the neutral lipids were subjected to conventional liquid chromatography (ODS column, mobile phase: acetone:acetonitrile=3:2, refractive index (RI) detector) to separate them into the molecular species (FIG. 5). After the separation, each of the molecular species was hydrolyzed and methyl-esterified, and the fatty acid residues were determined by gas chromatography.

The results of the analysis are as follows.

TABLE 10

Analysis of triglycerides in neutral lipid

| Peak No. | Molecular species | Quantitative ratio (%) |
|---|---|---|
| 1 | 14:0–16:0–16:0 | 3.4 |
| 2 | 16:0–16:0–16:0 | 8.0 |
| 3 | 14:0–16:0–22:6 | 4.0 |
| 4 | 16:0–16:0–22:5 | 7.8 |
| 5 | 16:0–16:0–22:6 | 27.4 |
| 6 | 16:0–22:5–22:6 | 8.4 |
| 7 | 16:0–22:6–22:6 | 16.9 |

The seven triglycerides constitute 70% by weight or more of all the triglycerides. Of these triglycerides, the molecular species contained in the largest amount is 16:0—16:0—22:6 species, which constitutes about 27% by weight of all the triglycerides.

Example 9

Determination of Positions in Triglycerides at Which Are Attached

Figure 6:
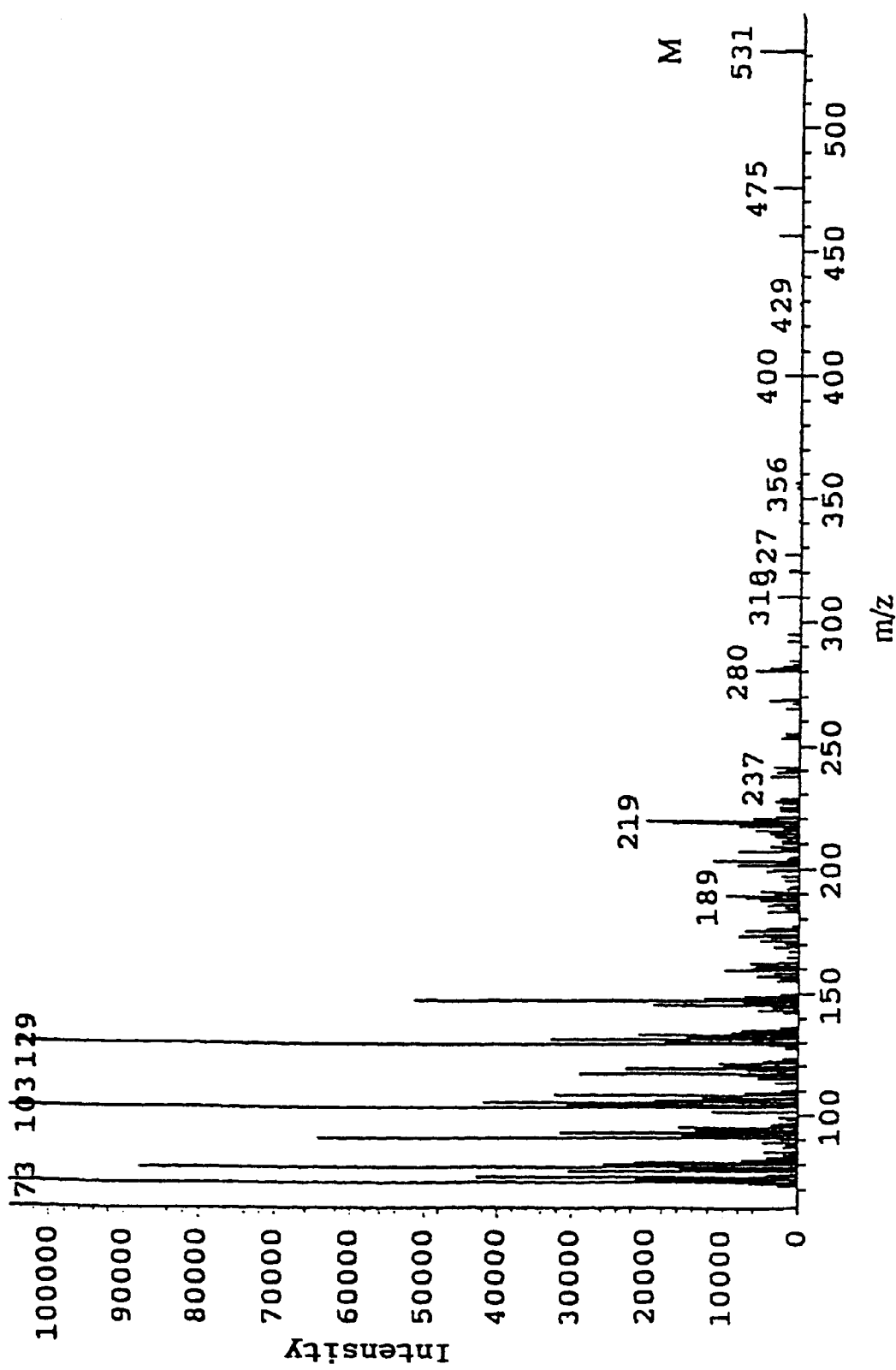
FIG. 6 is a chart showing the results obtained by lipase-treating the triglyceride (molecular species 16:0—16:0—22:6) derived from the Schizochytrium genus SR21 strain, trimethylsilylating the resultant and then carrying out GC/MS measurement.

After drying the triglyceride (molecular species: 16:0—16:0—22:6) fractionated in Example 8, it was treated with a lipase which is specific to the 1- and 3-positions. Then, the resulting 2-monoglyceride was trimethylsilylated, and the fatty acid residue was determined by GC/MS. The lipase treatment was carried out at 35° C. for 30 minutes using 2 ml of 50 mM acetate buffer (pH 5.5) and 1000 units of lipase. After the reaction, the reaction mixture was extracted with diethyl ether and the 2-monoglyceride was trimethylsilylated using a commercially available trimethylsilylating agent. The result is shown in FIG. 6 and a fragment peak was obtained which corresponded to the molecular weight of a monoglyceride having the 22:6 fatty acid attached, and it was found that the triglyceride was 16:0—22:6—16:0 species in which the residue of the 22:6 fatty acid was attached to the 2-position of the glycerol backbone.

Example 10

Influence of the Concentration of Nitrogen

Firstly, 60 g of glucose, 3 g of potassium dihydrogen phosphate and 0.5 g of corn steep liquor per liter of medium were added to a ½ concentration of an artificial sea water medium, after which ammonium sulfate was added to the resulting medium in the concentration as shown in Table 11. Then, 3 L of the medium thus prepared was charged into a 5 L volume jar fermenter, after which 60 ml of a pre-culture prepared in a similar manner to that described in Example 5 was added to the medium and cultivation was carried out under the conditions of 28° C., 1 vvm., 300 rpm and pH 4.0.

After the consumption of glucose, 100 ml of the cultured medium was taken and cell bodies were collected by centrifugation. The cell bodies were washed and freeze-dried to obtain dried cell bodies, which were weighed to determine the amount of cell bodies per liter of medium.

Next, the amount of cell bodies per liter of medium, the percent content of total fatty acids per liter of medium, and the amount of DHA and DPA per liter of medium were determined in a similar manner to that described in Example 5. These results are shown in Table 11.

TABLE 11

| | Results of analysis | | | | | | |
|---|---|---|---|---|---|---|---|
| $(NH_4)_2SO_4$ | Amount of cell bodies (g) | Total amount of fatty acids (g) | Percent content of fatty acids (wt %) | Percent content of DHA (wt %) | Amount of DHA (g) | Percent content of DPA (wt %) | Amount of DPA (g) |
| 0.5 | 6.5 | 4.8 | 74.5 | 31.4 | 1.5 | 7.9 | 0.38 |
| 1.0 | 8.6 | 6.0 | 69.8 | 32.0 | 1.9 | 8.0 | 0.48 |
| 2.0 | 15.3 | 9.1 | 59.6 | 35.0 | 3.2 | 8.8 | 0.81 |
| 3.0 | 20.5 | 10.7 | 52.2 | 35.8 | 3.8 | 8.9 | 0.90 |

A good growth was observed when the concentration of ammonium sulfate was between 2.0 and 3.0 g/L. In addition, the percent content of fatty acids increased to 70% or more when the concentration of ammonium sulfate was between 0.5 and 1.0 g/L.

Example 11

Influence of Organic and Inorganic Nitrogen Sources

Firstly, 60 g of glucose, 3 g of potassium dihydrogen phosphate and 0.5 g of corn steep liquor per liter of medium were added to a ½ concentration of an artificial sea water medium, after which corn steep liquor (CSL) as an organic nitrogen source and ammonium sulfate as an inorganic nitrogen source were added to the resulting medium at the concentrations shown in Table 12, and while the ratio of these two nitrogen sources varied the concentration of total nitrogen sources was maintained at a constant level. Then, 3 L of the medium thus prepared was charged into a 5 L volume jar fermenter, after which 60 ml of a pre-culture prepared in a similar manner to that described in Example 5 was added to the medium and cultivation was carried out under the same conditions as in Example 5.

After the consumption of glucose, 100 ml of the cultured medium was taken and cell bodies were collected by centrifugation. The cell bodies were washed and freeze-dried to obtain dried cell bodies, which were weighed to determine the amount of cell bodies per liter of medium. These results are shown in Table 12.

Next, the amount of cell bodies per liter of medium, the percent content of total fatty acids per liter of medium, and the amount of DHA and DPA per liter of medium were determined in a similar manner to that described in Example 5. These results are shown in Table 12.

TABLE 12

Results of analysis

| Exp. No. | CSL (g) | Ammonium sulfate (g) | Amount of cell bodies (g) | Total amount of fatty acids (g) | Percent content of fatty acids (%) | Percent content of DHA (wt %) | Amount of DHA (g) | Percent content of DPA (wt %) | Amount of DPA (g) |
|---|---|---|---|---|---|---|---|---|---|
| 501 | 0.7 | 2.0 | 21.0 | 14.8 | 70.5 | 31.8 | 4.7 | 8.1 | 1.2 |
| 502 | 2.0 | 1.7 | 20.0 | 13.7 | 68.5 | 31.7 | 4.3 | 7.3 | 1.0 |
| 503 | 3.3 | 1.3 | 23.2 | 14.5 | 62.4 | 30.7 | 4.5 | 6.9 | 1.0 |
| 504 | 5.3 | 0.7 | 21.0 | 13.7 | 68.5 | 29.9 | 4.3 | 8.0 | 1.1 |
| 505 | 8.0 | 0 | 20.6 | 13.4 | 65.2 | 27.9 | 3.8 | 6.7 | 0.9 |

A good growth was observed in all compositions and the present strain could grow by consuming organic and inorganic nitrogen sources without selecting either one of them. In addition, there was little difference in the productivity of DHA and DPA.

Example 12

High Concentration Cultivation

Firstly, 3 g of potassium dihydrogen phosphate per liter of medium was added to a ½ concentration of an artificial sea water medium, after which glucose, corn steep liquor and ammonium sulfate were added to the resulting medium at the concentration as shown in Table 13. Then, 3 L of the medium thus prepared was charged into a 5 L volume jar fermenter and cultivation was carried out under the culture conditions as shown in Example 5.

After the consumption of glucose, 100 ml of the cultured medium was taken and cell bodies were collected by centrifugation. The cell bodies were washed and freeze-dried to obtain dried cell bodies, which were weighed to determine the amount of cell bodies per liter of medium.

Next, the amount of cell bodies per liter of medium, the total amount of fatty acids per liter of medium, the percent content of fatty acids per dried cell bodies, the percent content of DHA and DPA per total fatty acids, and the amount of DHA and DPA per liter of medium were determined in a similar manner to that described in Example 5. These results are shown in Table 13.

From these results, it has become apparent that cultivation of the present strain under the increased concentration of carbon and nitrogen sources leads to the increase of the production yield of DHA and DPA in proportion to the increase of the concentration of glucose.

Example 13

Influence of Agitation Rate

Cultivation was carried out under the same medium composition and culturing conditions as shown in Example 5, using agitation rates of 100 and 300 rpm in a fermenter. The time spent in consuming glucose was about 100 hours at an agitation rate of 100 rpm, while it became about half, i.e. 50 to 60 hours at an agitation rate of 300 rpm. On the other hand, the amount of fatty acids and the amount of DHA and DPA per liter of medium were a little higher when cultivation was carried out at the agitation rate of 300 rpm (Table 14).

TABLE 13

Results of analysis

| Exp. No. | Amount of glucose (g) | Amount of CSL (g) | Amount of ammonium sulfate (g) | Culturing time (hours) | Amount of dried cell bodies (g) | Total amount of fatty acids (g) | Percent content of fatty acids (wt %) | Percent content of DHA (wt %) | Amount of DHA (g) | Percent content of DPA (wt %) | Amount of DPA (g) |
|---|---|---|---|---|---|---|---|---|---|---|---|
| 601 | 60 | 0.7 | 2.0 | 60 | 21.9 | 14.8 | 67.6 | 34.5 | 5.11 | 6.8 | 1.01 |
| 602 | 80 | 0.93 | 2.7 | 84 | 32.0 | 21.9 | 68.6 | 34.7 | 7.62 | 7.1 | 1.55 |
| 603 | 100 | 1.17 | 3.3 | 92 | 37.7 | 31.15 | 82.6 | 33.3 | 10.37 | 6.3 | 2.03 |
| 604 | 120 | 1.4 | 4.0 | 108 | 48.1 | 37.3 | 77.5 | 35.6 | 13.26 | 7.4 | 2.76 |
| 605 | 150 | 1.75 | 5 | 120 | 59.2 | 41.6 | 70.3 | 37.3 | 15.52 | 8.2 | 3.43 |

TABLE 14

Results of analysis

| Revolutions (rpm) | Amount of cell bodies (g) | Total amount of fatty acids (g) | Percent content of fatty acids (%) | Percent content of DHA (%) | Amount of DHA (g) | Percent content of DPA (%) | Amount of DPA (g) |
|---|---|---|---|---|---|---|---|
| 100 | 15.3 | 9.1 | 59.6 | 35.0 | 3.2 | 8.4 | 0.76 |
| 300 | 20.5 | 10.7 | 52.2 | 35.8 | 3.9 | 8.5 | 0.91 |

Example 14

The cultured medium prepared according to Example 12 was collected, the liquid components were removed with a filter press, and the residue was dried to obtain 10 kg of cell bodies containing 10% moisture. According to a conventional method, the cell bodies were extracted with hexane to obtain a hexane solution, from which hexane was removed to obtain 5.9 kg of a fat. On the other hand, the cell bodies after the hexane extraction were dried to remove hexane, by which 3.9 kg of post-extraction cell bodies were obtained. The above fat contained 35% of DHA and 8% of DPA, and the post-extraction cell bodies contained 1.2% of DHA and 0.3% of DPA.

Example 15

Laying hens (Izabrown species) of 200 feeding days were divided into two groups, each group containing five hens. One group was a control group and the hens of the group were fed for 25 days with a conventional feedstuff. The other group was an experimental group and the hens of the group were fed for 25 days with the conventional feedstuff to which 5 g of the fat obtained in Example 14 was added every day.

On the 25th day, the weight of three eggs and yolks, the concentration of DHA and DPA, as well as the gloss and taste of the yolk were measured. The results are shown in Table 15. It is apparent that the percent content of DHA and DPA in the yolk clearly increases by feeding the hens with a feedstuff containing the fat. Also, it is possible to obtain a yolk having a good gloss and melting feeling.

TABLE 15

|  | Experimental group | Control group |
|---|---|---|
| Weight of egg (three eggs) (g) | 213 | 211 |
| Weight of yolk (g) | 55 | 52 |
| DHA (%) | 3.5 | 1.5 |
| DPA (%) | 0.8 | trace |
| Gloss of yolk | good gloss | rough feeling |
| Taste of yolk | melting feeling | watery feeling |

Example 16

Laying hens (Izabrown species) of 200 feeding days were divided into two groups. One group was a control group and five hens of the group were fed for 25 days with a conventional feedstuff. The other group was an experimental group and three hens of the group were fed for 25 days with a feedstuff prepared by reducing 50 g of the conventional feedstuff from that given to the control group and instead adding 50 g of the post-extraction cell bodies obtained in Example 14 to the residual conventional feedstuff.

On the 25th day, the weight of three eggs and yolks, the concentration of DHA and DPA, as well as the gloss and taste of the yolk were measured. The results are shown in Table 16. It is apparent that the percent content of DHA and DPA in the yolk clearly increases by feeding the hens with a feedstuff containing the post-extraction cell bodies. Also, it is possible to obtain a yolk having a good gloss and melting feeling.

TABLE 16

|  | Experimental group | Control group |
|---|---|---|
| Weight of egg (three eggs) (g) | 212 | 211 |
| Weight of yolk (g) | 53 | 52 |
| DHA (%) | 2.1 | 1.5 |
| DPA (%) | 0.2 | trace |
| Gloss of yolk | good gloss | rough feeling |
| Taste of yolk | melting feeling | watery feeling |

Example 17

Preparation of a Milk Containing the (n-6) Series of Docosapentaenoic Acid and DHA A milk containing the (n-6) series of docosapentaenoic acid and DHA was prepared by mixing 6 g of a yolk oil containing the (n-6) series of docosapentaenoic acid and DHA [containing 0.8% of the (n-6) series of docosapentaenoic acid and 3.5% of DHA] with 100 g of a powdered milk, the yolk oil being extracted from the yolk obtained in Example 15 according to a conventional method. The milk contained 0.19% of the (n-6) series of docosapentaenoic acid and 0.84% of DHA based on the total fatty acids contained in the milk. Thus, it is possible to modify a milk preparation so that the amount of the (n-6) series of docosapentaenoic acid and DHA, which are insufficient in a conventional milk preparation, resembles that in human milk.

Example 18

Preparation of a Milk Containing the (n-6) Series of Docosapentaenoic Acid and DHA The crude fat extracted in Example 7 was conventionally divided into neutral and polar lipids by liquid/liquid distribution with hexane and 90% methanol to obtain a neutral lipid containing the (n-6) series of docosapentaenoic acid and DHA [containing 7.9% of the (n-6) series of docosapentaenoic acid and 33.7% of DHA]. Then, a milk containing the (n-6) series of docosapentaenoic acid and DHA was prepared by mixing 0.6 g of the above oil with 100 g of a powdered milk. The milk contained 0.19% of the (n-6) series of docosapentaenoic acid and 0.80% of DHA based on the total fatty acids contained in the milk. Thus, it is possible to modify a milk preparation so that the amount of the (n-6) series of docosapentaenoic acid and DHA, which are insufficient in conventional milk preparations, resembles that in human milk.

Example 19

Preparation of Capsules Containing the (n-6) Series of Docosapentaenoic Acid and DHA

TABLE 17

| Capsule | |
| --- | --- |
| Gelatin | 70.0% |
| Glycerin | 22.9% |
| Methyl para-hydroxybenzoate | 0.15% |
| Propyl para-hydroxybenzoate | 0.51% |
| Water | balance |
| Total | 100% |

Soft capsules were prepared by the conventional filling of soft capsule receptacles composed of the above components with 300 mg of a microorganism oil containing the (n-6) series of docosapentaenoic acid and DHA obtained in Example 12.

Example 20

Preparation of a Drink Containing the (n-6) Series of Docosapentaenoic Acid and DHA Fifty grams of commercially available plain yogurt, 50% of the microorganism oil containing the (n-6) series of docosapentaenoic acid and DHA obtained in Example 12 and 1 g of β-cyclodextrin were charged into a vessel, and the mixture was stirred for about 3 minutes and emulsified to obtain an emulsion in which W/O/W, O/W/O and other types were intermingled.

Example 21

Preparation of a Bait for Bait-microorganisms Containing DHA and DPA

The cultured medium prepared according to Example 5 was collected, and liquid components were removed with a filter press to obtain cell bodies. The resulting cell bodies were dried by heating to 105° C. for 3 hours, and the dried cell bodies were powdered with a coffee mill. Using the resulting powder or using baker's yeast as a control, cultivation of rotifer and brine shrimp was carried out.

The cultivation procedures are as follows. Thus, 200 L of sea water was charged into a 300 L volume of a water tank, 100 rotifers per milliliter or 20 brine shrimps per milliliter were released into the tank, and cultivation was carried out at 23° C. under an aeration condition giving the above powder of cell bodies or baker's yeast as a bait in an amount of 1 g/$10^6$ rotifers/day and 1 g/$10^5$ brine shrimps/day, respectively. The rotifers and brine shrimps grew by ingesting the baits. Sampling was carried out on the third day, and the composition of the fatty acids contained in the bait-microorganisms was determined to obtain the results as shown in Tables 18 and 19.

As shown by the results, the powder of cell bodies gave a better result than the baker's yeast in the accumulation of DHA and DPA both in rotifers and brine shrimps.

TABLE 18

| Rotifer | Fatty acid composition (%) | |
| --- | --- | --- |
|  | DHA | DPA |
| Control (baker's yeast) | 0 | 0 |
| Test (SR 21 strain) | 26 | 5 |

TABLE 19

| Brine shrimp | Fatty acid composition (%) | |
| --- | --- | --- |
|  | DHA | DPA |
| Control (baker's yeast) | 0 | 0 |
| Test (SR 21 strain) | 23 | 4 |

INDUSTRIAL APPLICABILITY

The marine microorganisms according to the present invention are superior in their proliferation character and their propensity to produce fat, have the ability to produce the (n-3) series of DHA and the (n-6) series of DPA very well, and produce very little EPA. Accordingly, using the microorganisms according to the present invention, it is possible to produce a fat containing the (n-3) series of DHA and the (n-6) series of DPA in a high content but containing EPA in a low content, which is useful in the fields of foods and pharmaceuticals, in a high yield. It is also possible to separate the (n-3) series of DHA and the (n-6) series of DPA having a high purity from the fat.

Also, since the fat composition of the present invention contains the (n-6) series of DPA in addition to the (n-3) series of DHA having various physiological activities at a certain ratio, it is possible to stably and effectively supply the (n-6) series of DPA and the (n-3) series of DHA to subjects in need of these highly unsaturated fatty acids by adding the present fat composition to various products (milk preparations for babies, milk preparations for premature babies, foods for children, foods for the old, foods for supplementing nutrients, functional foods, transintestinal nutritives, feedstuffs for animals, feed premixes for animals, baits for bait-microorganisms, etc.). In particular, the above feedstuffs for animals, feed premixes for animals and baits for bait-microorganisms can be produced much more economically because the post-extraction residue of the cultured cell bodies containing DHA and DPA or the like can be used for these products. In addition, it is also possible to obtain eggs of domestic fowl or a yolk oil previously never seen, in which DHA and/or DPA are enhanced, by giving the above feedstuffs for animals to the domestic fowl.

We claim:

1. A process for preparing a fat composition containing a member selected from the group consisting of the (n-3) series of docosahexaenoic acid and the (n-6) series of docosapentaenoic acid, which process comprises culturing the Schizochytrium genus SR21 strain (FERM BP-5034), which has the ability to produce a fat composition containing at least 15% by weight of the (n-3) series of docosahexaenoic acid, at least 5% by weight of the (n-6) series of docosapentaenoic acid, and at most 2% and greater than zero percent by weight of the (n-3) series of eicosapentanoic acid per total fatty acids in the fat composition, in the medium and recovering said fat composition from the culture.

2. A process according to claim 1 for preparing the (n-3) series of docosahexaenoic acid which comprises isolating the (n-3) series of docosahexaenoic acid from the fat composition containing the (n-3) series of docosahexaenoic acid and the (n-6) series of docosapentaenoic acid.

3. A process according to claim 1 for preparing the (n-6) series of docosapentaenoic acid which comprises isolating the (n-6) series of docosapentaenoic acid from the fat composition containing the (n-3) series of docosahexaenoic acid and the (n-6) series of docosapentaenoic acid.

4. A fat composition which is the same as that obtained according to claim 1 by culturing the Schizochytrium genus SR21 strain (FERM BP-5034), which has the ability to produce the (n-3) series of docosahexaenoic acid and the (n-6) series of docosapentaenoic acid.

5. A fat composition according to claim 4 which is the same as that contained in a culture or a sterilized culture in the course of producing the fat composition by cultivation of a microorganism, or a culture or a sterilized culture at the end of cultivation, or cultured cell bodies collected from any culture or dried cell bodies, or a residue obtained after recovering the fat composition from any culture.

6. A fat composition according to claim 4 which contains at least 1% of the (n-6) series of docosapentaenoic acid based on the weight of total fatty acids.

7. A fat composition according to claim 4 which contains at most 2% and more than 0% of the (n-3) series of eicosapentaenoic acid based on the weight of total fatty acids.

8. A fat composition according to claim 4 which contains 3 to 6 parts by weight of the (n-3) series of docosahexaenoic acid per one part by weight of the (n-6) docosapentaenoic acid.

9. A fat composition according to claim 4 which is a neutral lipid.

10. A fat composition according to claim 4 which contains glycerides wherein the (n-3) series of docosahexaenoic acid is attached to only the 2-position of glycerin.

11. A fat composition according to claim 4 which contains glycerides wherein the (n-3) series of docosahexaenoic acid is attached to the 1- and 2-positions or the 1- and 3-positions of glycerin.

12. A fat composition according to claim 9 wherein 85% by weight or more of the neutral lipid is triglycerides.

13. A food for supplementing nutrients which contains a fat composition according to claim 4.

14. A food for supplementing nutrients according to claim 13 wherein the fat composition is encapsulated in gelatin capsules.

15. A food for supplementing nutrients according to claim 13 which is a food or drink in the form of a liquid, granules or tablets containing a fat composition according to claim 4.

16. A milk preparation for babies which contains a fat composition according to claim 4.

17. A milk preparation for premature babies which contains a fat composition according to claim 4.

18. A food for children which contains a fat composition according to claim 4.

19. A food for the old which contains a fat composition according to claim 4.

20. A transintestinal nutritive which contains a fat composition according to claim 4.

21. A feedstuff for animals which contains a fat composition according to claim 4.

22. A feed premix for animals which contains a fat composition according to claim 4.

23. A bait for bait-microorganisms which contains a fat composition according to claim 4.

24. A process for preparing a fat composition containing the (n-3) series of docosahexaenoic acid and the (n-6) series of docosapentaenoic acid, which process comprises culturing a microorganism which is of a strain which belongs to the same species as that of the Schizochytrium genus SR21 strain (FERM BP-5034), which has the ability to produce a fat composition containing at least 15% by weight of the (n-3) series of docosahexaenoic acid, at least 5% by weight of the (n-6) series of docosapentaenoic acid and at most 2% and greater than 0% by weight of the (n-3) series of eicosapentaenoic acid, per total fatty acids in said fat composition, in a medium and recovering said fat composition from the culture.

25. A process according to claim 24, which comprises culturing a microorganism which has the ability to produce a fat composition containing at most 0.5% by weight of the (n-3) series of eicosapentaenoic acid per total fatty acids in said fat composition.

26. A process for preparing a fat composition containing the (n-3) series of docosahexaenoic acid and the (n-6) series of docosapentaenoic acid, which process comprises culturing a microorganism which is of a strain which belongs to the same species as that of the Schizochytrium genus SR21 strain (FERM BP-5034), which has the ability to produce a fat composition containing at least 15% by weight of the (n-3) series of docosahexaenoic acid, at least 4% by weight of the (n-6) series of docosapentaenoic acid and at most 0.5% and greater than 0% by weight of the (n-3) series of eicosapentaenoic acid, per total fatty acids in said fat composition, in a medium and recovering said fat composition from the culture.

27. A fat composition containing the (n-3) series of docosahexaenoic acid and the (n-6) series of docosapentaenoic acid, which is the same as that obtained according to claim 24 by culturing a microorganism belonging to the same species as that of the Schizochytrium genus SR21 strain (FERM BP-5034), which has the ability to produce a fat containing at least 15% by weight of the (n-3) series of docosahexaenoic acid, at least 5% by weight of the (n-6) series of docosapentaenoic acid and at most 2% and greater than 0% by weight of the (n-3) series of eicosapentaenoic acid, per total fatty acids in said fat.

28. A fat composition according to claim 27, which is obtained by culturing a microorganism which has the ability to produce a fat composition containing at most 0.5% by weight of the (n-3) series of eicosapentaenoic acid per total fatty acids in said fat composition.

29. A fat composition containing the (n-3) series of docosahexaenoic acid and the (n-6) series of docosapentaenoic acid, which is the same as that obtained according to claim 26 by culturing a microorganism belonging to the same species as that of the Schizochytrium genus SR21 strain (FERM BP-5034), which has the ability to produce a fat containing at least 15% by weight of the (n-3) series of docosahexaenoic acid, at least 4% by weight of the (n-6) series of docosapentaenoic acid and at most 0.5% by weight of the (n-3) series of eicosapentaenoic acid, per total fatty acids in said fat.

30. A fat composition according to claim 27 which is the same as that contained in a culture or a sterilized culture in the course of producing the fat composition by cultivation of a microorganism, or a culture or a sterilized culture at the end of cultivation, or cultured cell bodies collected from any culture or dried cell bodies, or a residue obtained after recovering the fat composition from any culture.

31. A fat composition according to claim 27 which contains 3 to 6 parts by weight of the (n-3) series of docosahexaenoic acid per one part by weight of the (n-6) series of docosapentaenoic acid.

32. A fat composition according to claim 27 which is a neutral lipid.

33. A fat composition according to claim 27 which contains glycerides wherein the (n-3) series of docosahexaenoic acid is attached to only the 2-position of glycerin.

34. A fat composition according to claim 27 which contains glycerides wherein the (n-3) series of docosahexaenoic acid is attached to the 1- and 2-positions or the 1- and 3-positions of glycerin.

35. A fat composition according to claim 32 wherein 85% by weight or more of the neutral lipid is triglycerides.

36. A food for supplementing nutrients which contains a fat composition according to claim 27.

37. A food for supplementing nutrients according to claim 36 wherein the fat composition is encapsulated in gelatin capsules.

38. A food for supplementing nutrients according to claim 36 which is a food or drink in the form of a liquid, granules or tablets.

39. A milk preparation for babies which contains a fat composition according to claim 27.

40. A milk preparation for premature babies which contains a fat composition according to claim 27.

41. A food for children which contains a fat composition according to claim 27.

42. A food for the old which contains a fat composition according to claim 27.

43. A transintestinal nutritive which contains a fat composition according to claim 27.

44. A feedstuff for animals which contains a fat composition according to claim 27.

45. A feed premix for animals which contains a fat composition according to claim 27.

46. A bait for bait-microorganisms which contains a fat composition according to claim 27.

* * * * *